(12) United States Patent
Wigler et al.

(10) Patent No.: US 6,569,617 B1
(45) Date of Patent: *May 27, 2003

(54) METHODS FOR IDENTIFYING MODULATORS OF GENE EXPRESSION

(75) Inventors: Michael H. Wigler, Lloyd Harbor, NY (US); John J. Colicelli, Huntington, NY (US)

(73) Assignee: Cold Spring Harbor Laboratory, Cold Spring, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/471,884

(22) Filed: Jun. 7, 1995

Related U.S. Application Data

(62) Division of application No. 07/511,715, filed on Apr. 20, 1990, now Pat. No. 6,080,540.

(51) Int. Cl.$^7$ .............................. C12Q 1/68; C12N 5/10; C12N 15/63

(52) U.S. Cl. ........................... 435/6; 435/7.1; 435/69.1; 435/325; 435/455; 435/254.2; 435/254.11

(58) Field of Search .......................... 435/4, 6, 7.1, 7.4, 435/29, 172.1, 172.3, 325, 254.1, 254.11, 69.1, 455, 252.3, 243

(56) References Cited

U.S. PATENT DOCUMENTS

| 5,482,835 A | | 1/1996 | King et al. ..................... 435/6 |
| 6,080,540 A | * | 6/2000 | Wigler et al. .................. 435/6 |

FOREIGN PATENT DOCUMENTS

| WO | WO89/07654 | 8/1989 |

OTHER PUBLICATIONS

Adams et al., "Sequence Identification of 2,375 Human Brain Genes," *Nature*, 355:632–634 (Feb. 13, 1992).
Altman et al., "A Mammalian Translation Initiation Factor Can Substitute for Its Yeast Homologue in Vivo," *J. Biol. Chem.*, 264(21):12145–12147 (Jul. 25, 1989).
Ammerer, G., "Expression of Genes in Yeast Using the ADCI Promoter," *Meth. Enzymol.*, 101:192–201 (1983).
Baecker et al., "Isolation of a cDNA Encoding a Human Rolipram–Sensitive Cyclic AMP Phosphodiesterase (PDE IV$_D$)," *Gene*, 138(1–2):253–256 (Jan. 28, 1994).
Ballester et al., "Genetic Analysis of Mammalian GAP Expressed in Yeast," *Cell*, 59:681–686 (Nov. 17, 1989).
Barbacid, M., "ras Genes," *Ann. Rev. Biochem.*, 56:779–827 (1987).
Beavo, "Multiple Phosphodiesterase Isozymes Background, Nomenclature and Implications", In: *Cyclic Nucleotide Phosphodiesterases: Structure, Regulation and Drug Action*, Chapter 1, Beavo, J. and Houslay, M.D., (eds.), John Wiley & Sons, New York. pp. 3–15 (1990).

Beavo, J.A., "Multiple Isozymes of Cyclic Nucleotide Phosphodiesterase," *Advances in Second Messenger and Phosphoprotein Research, vol. II*, Greengard et al., (eds.), Raven Press, New York, pp. 1–38 (1988).
Beavo et al., "Primary Sequence of Cyclic Nucleotide Phosphodiesterase Isozymes and the Design of Selective Inhibitors," *TIPS (Reviews)*, 11:150–155 (1990).
Beckner et al., "The ras Oncogene Product p21 is not a Regulatory Component of Adenylate Cyclase," *Nature*, 317:71 (Sep. 5, 1985).
Bennetzen et al., "The Primary Structure of the *Saccharomyces cerevisiae* Gene for Alcohol Dehydrogenase I," *J. Biol. Chem.*, 257(6):3018–3025 (Mar. 25, 1982).
Biggin et al., "Buffer Gradient Gels and $^{35}$S Label as an Aid to Rapid DNA Sequence Determination," *Proc. Nat'l Acad. Sci., USA*, 80:3963–3965 (Jul., 1983).
Birchmeier et al., "RAS Proteins Can Induce Meiosis in Xenopus Oocytes," *Cell*, 43:615–621 (Dec., 1985).
Bolger et al., "A Family of Human Phosphodiesterases Homologous to the dunce Learning and Memory Gene Product of *Drosophila melanogaster* Are Potential Targets for Antidepressant Drugs," *Mol. & Cell. Biol.*, 13(10):6558–6571 (Oct., 1993).
Bradford, M.M., "A Rapid and Sensitive Method for the Quantitation of Microgram Quantities of Protein Utilizing the Principle of Protein–Dye Binding," *Anal. Biochem.* 72:248–254 (1976).
Brugge et al., "Expression of Rous Sarcoma Virus Transforming Protein pp60$^{v-src}$ in *Saccharomyces cerevisiae* Cells," *Mol. & Cell. Biol.*, 7(6):2180–2187 (Jun., 1987).
Camonis et al., "Of Mice and Yeast: Versatile Vectors Which Permit Gene Expression in Both Budding Yeast and Higher Eukaryotic Cells," *Gene*, 86:263–268 (1990).

(List continued on next page.)

*Primary Examiner*—David Guzo
(74) *Attorney, Agent, or Firm*—Marshall, Gerstein & Borun

(57) ABSTRACT

A method of cloning mammalian genes encoding proteins which can function in microorganisms, particularly yeast, and can modify, complement, or suppress a genetic defect associated with an identifiable phenotypic alteration or characteristic in the microorganism. It further relates to mammalian genes cloned by the present method, as well as to products encoded by such genes and antibodies-which can bind the encoded proteins. More specifically, the present invention relates to a method of cloning mammalian genes which encode products which modify, complement or suppress a genetic defect in a biochemical pathway in which cAMP participates or in a biochemical pathway which is controlled, directly or indirectly, by a RAS protein, to products (RNA, proteins) encoded by the mammalian genes cloned in this manner and to antibodies which can bind the encoded proteins.

1 Claim, 18 Drawing Sheets

OTHER PUBLICATIONS

Capon et al., "Activation of Ki–ras 2 Gene in Human Colon and Lung Carcinomas by Two Different Point Mutations," *Nature*, 304:507–513 (Aug., 1983).

Capon et al., "Complete Nucleotide Sequences of the T24 Human Bladder Carcinoma Oncogene and Its Normal Homologue," *Nature*, 302:33–37 (Mar. 3, 1983).

Chang et al., "Phenotypic Expression in *E. coli* of a DNA Sequence Coding for Mouse Dihydrofolate Reductase," *Nature*, 275:617–624 (Oct. 19, 1978).

Charbonneau et al., "Identification of a Conserved Domain Among Cyclic Nucleotide Phosphodiesterases From Diverse Species," *Proc. Natl. Acad. Sci., USA*, 83:9308–9312 (Dec., 1986).

Chen et al., "Molecular Analysis of cDNA Clones and the Corresponding Genomic Coding Sequences of the Drosophila Dunce[+] Gene, The Structural Gene for cAMP Phosphodiesterase," *Proc. Nat'l Acad. Sci., USA*, 83:9313–9317 (Dec., 1986).

Chirgwin et al., "Isolation of Biologically Active Ribonucleic Acid from Sources Enriched in Ribonuclease," *Biochem.*, 18:5294–5299 (1979).

Colicelli et al., "Expression of Three Mammalian cDNAs That Interfere With RAS Function in *Saccharomyces cerevisiae*," *Proc. Nat'l Acad. Sci., USA*, 88:2913–2917 (Apr., 1991).

Colicelli et al., "Isolation and Characterization of a Mammalian Gene Encoding a High–Affinity cAMP Phosphodiesterase," *Proc. Natl. Acad. Sci., USA*, 86:3599–3603 (May, 1989).

Davis, "Molecular Genetics of the Cyclic Nucleotide Phosphodiesterases", In: *Cyclic Nucleotide Phosphodiesterases: Structure, Regulation, and Drug Action*, Beavo, J. and Houslay, M.D., Eds.; John Wiley & Sons, New York, pp. 227–241 (1990).

Davis et al., "Cloning and Characterization of Mammalian Homologs of the Drosophila Dunce[+] Gene," *Proc. Nat'l. Acad. Sci., USA*, 86:3604–3608 (May, 1989).

Davis et al., "Dunce Mutants of *Drosophila melanogaster*: Mutants Defective in the Cyclic AMP Phosphodiesterase Enzyme System," *J. Cell. Biol.*, 90:101–107 (Jul., 1981).

Davis et al., "A Partial Characterization of the Cyclic Nucleotide Phosphodiesterases of *Drosophila melanogaster*," *Arch. Biochem. & Biophys.* 203(1):412–421 (1980).

Davis et al., "A Simple Direct Assay of 3',5'–Cyclic Nucleotide Phosphodiesterase Activity Based on the Use of Polyacrylamide–Boronate Affinity Gel Chromatography," *J. of Cyclic Nucleotide Research*, 5(1):65–74 (1979).

De Vos et al., "Three–Dimensional Structure of an Oncogene Protein: Catalytic Domain of Human c–H–ras p21," *Science*, 239:888–893 (Feb., 1988).

DeFeo–Jones et al., "ras–Related Gene Sequences Identified and Isolated from *Saccharomyces cerevisiae*," *Nature*, 306:707–709 (Dec., 1983).

DeFeo–Jones et al., "Mammalian and Yeast ras Gene Products: Biological Function in Their Heterologous Systems," *Science*, 228:179–184 (Apr. 12, 1985).

Dhar et al., "Nucleotide Sequence of Two ras[H] Related–Genes Isolated from the Yeast *Saccharomyces cerevisiae*," *Nucl. Acids Res.*, 12:3611–3618 (1984).

Dietzel & Kurjan, "The Yeast SCG1 Gene: A $G_\alpha$–like Protein Implicated in the a–and α–Factor Response Pathway," *Cell*, 50:10001–1010 (Sep. 25, 1987).

Dudai, Y., "Neurogenetic Dissection of Learning and Short Term Memory in Drosophila," *Ann. Rev. Neurosci.*, 11:537–563 (1988).

Eckmann et al., "Rolipram Major Depression: Results of a Double Blind Comparative Study With Amitriptyline," *Current Therapeutic Research*, 43(2):291–295 (Feb., 1988).

Ellis et al, "The p21 src Genes of Harvey and Kristen sarcoma viruses Originate from Divergent Members of a Family of Normal Vertebrate Genes," *Nature*, 292:506–511 (1981).

Faure et al., "Disruption of *Dictyostelium discoideum* Morphogenesis by Overproduction of cAMP Phosphodiesterae," *Proc. Nat'l Acad. Sci., USA*, 85:8076–8080 (Nov., 1988).

Field et al., "Mutations of the Adenylyl Cyclase Gene That Block RAS Function in *Saccharomyces cerevisiae*," *Science*, 247:464–467 (Jan., 1990).

Field et al., "Purification of a RAS–Repsonsive Adenylyl Cyclase Complex from *Saccharomyces cerevisiae* by Use of an Epitope Addition Method," *Mol. Cell. Biol.*, 8(5):2159–2165 (May, 1988).

Field et al., "Cloning and Characterization of CAP, the *S. cerevisiae* Gene Encoding the 70 kd Adenylyl Cyclase–Associated Protein," *Cell*, 61:319–327 (Apr. 20, 1990).

Fukui et al., "Molecular Cloning and Sequence Analysis of a ras Gene from *Schizosaccharomyces pombe*," *EMBO J.*, 4:687–691 (1985).

Fukui et al., "Role of a ras Homolog in the Life Cycle of *Schizosaccharomyces pombe*," *Cell*, 44:329–336 (Jan. 31, 1986).

Gerst et al., "CAP Is a Bifunctional Component of the *Saccharomyces cerevisiae* Adenylyl Cyclase Complex," *Mol. & Cell Biol.*, 11(3):1248–1257 (Mar., 1991).

Goddard et al., "Cloning of Human Purine–Nucleoside Phosphorylase cDNA Sequences by Complementation in *Escherichia coli*," *Proc. Nat'l Acad. Sci., USA*, 80:4281–4285 (Jul., 1983).

Goldner et al., "*Eine Neue Xanthin–Synthese*," *Ann. Chem.* 691:142–158 (1966).

Hanahan, D., "Studies on Transformation of *Escherichia coli* with Plasmids," *J. Mol. Biol.*, 166:557–580 (1983).

Hancock et al., "All ras Proteins Are Polyiosprenylated but Only Some Are Polmitoylated," *Cell*, 57:1167–1177 (Jun., 1989).

Henikoff et al., "Isolation of a Gene from Drosophila by Complementation in Yeast," *Nature*, 289:33–37 (Jan., 1981).

Hosaka et al., "Cloning of a Human Choline Kinase cDNA by Complementation of the Yeast cki Mutation," *FEBS 11157*, 304(2,3): 229–232 (Jun., 1992).

Hoshino et al., "A Human Homologue of the Yeast GST1 Gene Codes for a GTP–Binding Protein and is Expressed in a Proliferation–Dependent Manner in Mammalian Cells," *EMBO J.*, 8(12):3807–3814 (Dec., 1989).

Ito et al., "Transformation of Intact Yeast Cells Treated with Alkali Cations," *J. Bacteriol.*, 153:163–168 (Jan., 1983).

Jacquet et al., "A Fragment of *Dictyostelium discoideum* Genomic DNA That Complements the Ural Mutation of *Saccharomyces cerevisiae*," *J. Mol. Appl. Genet.*, 1(6):513–525 (1982).

Jin et al., "Characterization of the Structure of a Low $K_m$, Rolipram–sensitive cAMP Phosphodiesterase," *J. Biol. Chem.* 267(26):18929–18939 (Sep. 15, 1992).

Kataoka et al., "DNA Sequence and Characterization of the *S. cerevisiae* Gene Encoding Adenylate Cyclase," *Cell*, 43:493–505 (Dec., 1985).

Kataoka et al., "Functional Homology of Mammalian and Yeast RAS Genes," *Cell*, 40:19–26 (Jan., 1985).

Kataoka et al., "Genetic Analysis of Yeast RAS1 and RAS2 Genes," *Cell*, 37:437–445 (Jun., 1984).

Kitayama et al., "A ras–Related Gene with Transformation Suppressor Activity," *Cell* 56:77–84 (Jan., 1989).

Lee & Nurse, "Complementation Used to Clone a Human Homologue of the Fission Yeast Cell Cycle Control Gene cdc2," *Nature*, 327:31–35 (1987).

LeTrong et al., "Amino Acid Sequence of the Cyclic GMP Stimulated Cyclic Nucleotide Phosphodiesterase from Bovine Heart," *Biochemistry*, 29:10280–10288 (1990).

Livi et al., "Cloning and Expression of cDNA for a Human Low–$K^m$, Rolipram–Sensitive Cyclic AMP Phosphodiesterase," *Mol. Cell Biol.*, 10(6):2678–2686 (Jun., 1990).

Lizardi, P.M., "Methods for the Preparation of Messenger RNA," *Methods Enzymol.*, 96:24–38 (1983).

Lugnier et al., "Substituted Carbostyrils as Inhibitors of Cyclic AMP Phosphodiesterase," *Eur. J. Med. Chem.–Chim. Ther.*, 20:121–125 (1985).

Lundberg et al., "High–fidelity Amplification Using a Thermostable DNA Polymerase Isolated from *Pyrococcus furiosus*," *Gene*, 108:1–16 (1991).

Mandel et al., "Calcium–dependent Bacteriophage DNA Infection." *J. Mol. Biol.*, 53:159–162 (1970).

Martins et al., "Purification and Characterization of a Cyclic GMP–Stimulated Cyclic Nucleotide Phosphodiesterase from Bovine Tissues," *J. Biol. Chem.* 255(4):1973–1979 (Feb., 1982).

MacDonald et al., "Isolation of RNA Using Guanidinium Salts," *Meth. in Enzymol.* 152:219–227 (1983).

McGrath et al., "Comparative Biochemical Properties of Normal and Activated Human ras p21 Protein," *Nature*, 310:644–649 (Aug., 1984).

McHale et al., "Expression of Human Recombinant cAMP Phosphodiesterase Isozyme IV Reverse Growth Arrest Phenotypes in Phosphodiesterase–Deficient Yeast," *Mol. Pharmacol.*, 39:109–113 (1991).

McKnight & McConaughy, "Selection of Functional cDNAs by Complementation in Yeast," *Proc. Nat'l Acad. Sci., USA*, 80:4412–4416 (Jul., 1983).

McKnight et al., "Identification and Molecular Analysis of a Third *Aspergillus nidulans* Alcohol Dehydrogenase Gene," *EMBO J.*, 4(8):2093–2099 (1985).

McLaughlin et al., "A Low–$K_m$, Rolipram–sensitive, cAMP–specific Phosphodiesterase from Human Brain," *J. Biol. Chem.*, 268(9):6470–6476 (Mar. 25, 1993).

McLeod et al., "The Product of the mei3$^+$ Gene, Expressed Under Control of the Mating–Type Locus, Induces Meiosis and Sporulation in Fission Yeast," *EMBO J.*, 6(3):729–736 (1987).

Metzger et al., "The Human Oestrogen Receptor Functions in Yeast," *Nature*, 334:31–36 (Jul. 7, 1988).

Michaeli et al., "Isolation and Characterization of a Previously Undetected Human cAMP Phosphodiesterase by Complementation of cAMP Phosphodiesterase–deficient *Saccharomyces cerevisiae*," *J. Biol. Chem.*, 268(17:12925–12932 (1993).

Michaeli et al., "Mutants of H–ras that Interfere with RAS Effector Function in *Saccharomyces cerevisiae*," *EMBO J.*, 8:3039–3044 (1989).

Monaco et al., "Structure of Two Rat Genes Coding for Closely Related Rolipram–sensitive cAMP Phosphodiesterases," *J. Biol. Chem.*, 269(1):347–357 (Jan. 7, 1994).

Mortimer et al., "Yeast Genetics," *In: The Yeast, Chapter 8*, Donner Laboratory, University of California, Berkley, California 94720, U.S.A., and Department of Genetics, University of Washington, Seattle, Washington 98105, U.S.A., pp. 386–460 (1969).

Nakafuku et al., "Isolation of a Second Yeast *Saccharomyces cerevisiae* Gene (GPA2) Coding for Guanine Nucleotide–Binding Regulatory Protein: Studies on Its Structure and Possible Functions," *Proc. Nat'l Acad. Sci., USA*, 85:1374–1378 (Mar. 5, 1989).

Neuman–Silberberg et al., "The Drosophila ras Oncogenes: Structure and Nucleotide Sequence," *Cell*, 37: 1027–1033 (Jul., 1984).

Nicholson et al., "Differential Modulation of Tissue Function and Therapeutic Potential of Selective Inhibitors of Cyclic Nucleotide Phosphodiesterase Isoenzymes," *Trends in Pharm. Sci.* 12:19–27 (Jan., 1991).

Nikawa et al., "Cloning and Characterization of the Low–Affinity Cyclic AMP Phosphodiesterase Gene of *Saccharomyces cerevisiae*," *Mol. Cell. Biol.*, 7(10):3629–3636 (Oct. 1987).

Obernolte et al., "The cDNA of a Human Lymphocyte Cyclic–AMP Phosphodiesterase (PDE IV) Reveals a Multigene Family," *Gene*, 129:239–247 (1993).

Ovchinnikov et al., "Cyclic GMP Phosphodiesterae from Bovine Retina: Amino Acid Sequence of the α–Subunit and Nucleotide Sequence of the Corresponding cDNA," *FEBS 05223*, 223:169–173 (Oct., 1987).

Papageorge et al., "Comparative Biochemical Properties of p21 ras Molecules Coded for by Viral and Cellular ras Genes," *J. Virol.*, 44(2):509–519 (Nov., 1982).

Powers et al., "Dominant Yeast and Mammalian RAS Mutants That Interfere with the CDC25–Dependent Activation of Wild–Type RAS in *Saccharomyces cerevisiae*," *Mol. Cell. Biol.*, 9(2):390–395 (Feb., 1989).

Powers et al., "Genes in *S. cerevisiae* Encoding Proteins with Domains Homologous to the Mammalian ras Proteins," *Cell*, 36:607–612 (Mar., 1984).

Powers et al., "RAM, A Gene of Yeast Required for a Functional Modification of RAS Proteins and for Production of Mating Pheromone a–Factor," *Cell*, 47:413–422 (Nov., 1986).

Qui et al., "Characterization of the Memory Gene Dunce of *Drosophila melanogaster*," *J. Mol. Biol.*, 222:553–565 (1991).

Reddy et al., "A Point Mutation is Responsible for the Acquisition of Transforming Properties by the T24 Human Bladder Carcinoma Oncogene," *Nature*, 300:149–152 (Nov., 1982).

Repaske et al., "A Polymerase Chain Reaction Strategy to Identify and Clone Cyclic Nucleotide Phosphodiesterase cDNAs," *J. Biol. Chem.*, 267(26):18683–18688 (Sep. 15, 1992).

Reymond et al., "Development Regulation of a Dictyostelium Gene Encoding a Protein Homologous to Mammalian ras Protein," *Cell*, 39:141–148 (Nov., 1984).

Saiki et al., "Primer–Directed Enzymatic Amplification of DNA with a Thermostable DNA Polymerase," *Science*, 239:487–491 (Jan., 1988).

Sanger et al., "DNA Sequencing with Chain–Terminating Inhibitors," *Proc. Natl. Acad. Sci., USA*, 74:5463–5467 (Dec., 1977).

Sass et al., "Cloning and Characterization of the High–Affinity cAMP Phosphodiesterase of *Saccharomyces cerevisiae*," *Proc. Nat'l Acad. Sci., USA*, 83:9303–9307 (Dec., 1986).

Schacher et al., "Long–term Facilitation in Aplysia: Persistent Phosphorylation and Structural Changes," *Cold Spring Harbor Symp. on Quant. Biol., LV*:187–202 (1990).

Schuler et al., "A Workbench for Multiple Alignment Construction and Analysis," *Proteins: Struct. Funct. Genet.*, 9:180–190 (1991).

Shilo et al., "DNA Sequences Homologous to Vertebrate Oncogenes are Conserved in *Drosophila melanogaster*," *Proc. Natl'l Acad. Sci., USA* 78:6789–6792 (Nov., 1981).

Shimizu et al., "Structure of the Ki–ras Gene of the Human Lung Carcinoma Cell Line Calu–1," *Nature*, 304:497–500 (Aug., 1983).

Shimizu et al., "Three Human Transforming Genes are Related to the Viral ras Oncogenes," *Proc. Natl. Acad. Sci.*, 80:2112–2116 (Apr., 1983).

Short et al., "Lambda ZAP: A Bacteriophage Lambda Expression Vector With In Vitro Excision Properties," *Nucl. Acids Res.*, 16(15):7583–7600 (Aug., 1988).

Swinnen et al., "Molecular Cloning of Rat Homologues of the *Drosophila melanogaster* Dunce cAMP Phosphodiesterase: Evidence for a Family of Genes," *Proc. Nat'l Acad. Sci., USA*, 86:5325–5329 (Jul., 1989).

Swinnen et al., "Properties and Hormonal Regulation of Two Structurally Related cAMP Phosphodiesterases from the Rat Sertoli Cell," *J. Biol. Chem.*, 266(27):18370–18377 (Sep. 25, 1991).

Swinnen et al., "The mRNA Encoding a High–Affinity cAMP Phosphodiesterase if Regulated by Hormones and cAMP," *Proc. Nat'l Acad. Sci., USA*, 86:8197–8201 (Nov., 1989).

Tabin et al., "Mechanism of Activation of a Human Oncogene," *Nature*, 300:143–149 (Nov., 1982).

Taparowsky et al., "Activation of the T24 Bladder Carcinoma Transforming Gene is Linked to a Single Amino Acid Change," *Nature*, 300:762–765 (Dec., 1982).

Taparowsky et al., "Structure and Activation of the Human N–ras Gene," *Cell*, 34:581–586 (Sep., 1983).

Tempel et al., "Reward Learning in Normal and Mutant Drospophila," *Proc. Natl. Acad. Sci., USA*, 80:1482–1486 (Mar., 1983).

Thompson et al., "Identification of Type II (Cyclic GMP–Stimulatable) Cyclic Nucleotide Phosphodiesterase (CNPDE) mRNA in Rat Pheochromocytoma Cells (PC 12)," *FASEB J.*, 5(6):A1592 (Abstract 7092) (1991).

Toda et al., "Cloning and Characerization of BCY1, A Locus Encoding a Regulatory Subunit of the Cyclic AMP–Dependent Protein Kinase in *Saccharomyces cerevisiae*," *Mol. Cell. Biol.*, 7(4):1371–1377 (Apr., 1987).

Toda et al., "In Yeast, RAS Proteins Are Controlling Elements of Adenylate Cyclase," *Cell*, 40:27–36 (Jan., 1985).

Toda et al., "Exploring the Function of RAS Oncogenes by Studying the Yeast *Saccharomyces cerevisiae*," *Oncogenes and Cancer*, S.A. Aaronson et al., (Eds.), *Japan Sci. Soc. Press., Tokyo/VNU Sci. Press. Utrecht*, pp. 253–260 (1987).

Torphy et al., "Coexpression of Human cAMP–Specific Phosphodiesterase Activity and High Affinity Rolipram Binding in Yeast," *J. Biol. Chem.*, 267(3):1798–1804 (Jan. 25, 1992).

Trahey et al., "A Cytoplasmic Protein Stimulates Normal N–ras p21 GTPase, but Does Not Affect Oncogenic Mutants," *Science*, 238:542–545 (Oct., 1987).

Uno et al., "Characterization of Cyclic AMP–Requiring Yeast Mutants Altered in the Regulatory Subunit of Protein Kinase," *J. Biol. Chem.*, 257(23):14110–14115 (Dec., 1981).

Viera et al., "Production of Single–Stranded Plasmid DNA," *Methods in Enzymology*, 153:3–11 (1987).

Walter et al., "The Dunce Gene of Drosophila: Roles of $Ca^{2+}$ and Calmodulin in Adenosine 3':5'–Cyclic Monophosphate–Specific Phosphodiesterase Activity," *J. Neurosci.*, 4(2):494–501 (Feb., 1984).

Watson et al., "An Alternative Procedure for the Synthesis of Double–stranded cDNA for Cloning in Phage and plasmid Vectors," *In: DNA Cloning, A Practical Approach*, IRL Press, Oxford, pp. 79–88 (1984).

Wigler et al., "Studies of RAS Function in the Yeast *Saccharomyces cerevisiae*," *Cold Spring Harbor Symposium on Quant. Biol., LIII*:649–655 (1988).

Willingham et al., "Localization of the src Gene Product of the Harvey Strain of MSV to Plasma Membrane of Transformed Cells by Electron Microscopic Immunocytochemistry," *Cell*, 19:1005–1014 (Apr., 1980).

Wilson et al., "SRA5 Encodes the Low–$K_m$ Cyclic AMP Phosphodiesterase of *Saccharomyces cerevisiae*," *Mol. & Cell. Biol.*, 8(1):505–510 (Jan., 1988).

Xiong et al., "Human D–Type Cyclin," *Cell*, 65:691–699 (May 17, 1991).

Yeung et al., "Identification of Functional Murine Adenosine Deaminase cDNA Clones by Complementation in *Escherichia coli*," *J. Biol. Chem.*, 260:10299–10307 (Aug. 25, 1985).

Zhong et al., "Altered Synaptic Plasticity in Drosophila Memory Mutants with a Defective Cyclic AMP Cascade," *Science*, 251:198–201 (Jan. 11, 1991).

* cited by examiner

DPD
1

CTTGCGAATCGTAAGAAACAATTTCACC
CTGCTGACAAACCTTCACGGAGCACCGAACAAGAGGTCGCCAGCGGCTAGTCAGGCTCCAGTCACCAGACCTCCAAGAGAATCATATCAGAAACTAGCA
AGGAGACGCTGGAGGAACTAGACTGTGCCTAGACCCAGCCATCCAGACCTACCGCTCTGTCAGCGAGATGGCTTCAAACAAGTTCAAAGGATGGTG
ATGGAGACGCTGGAGGAACTAGACTGTGCCTAGACCCAGCCATCCAGACCTACCGCTCTGTCAGCGAGATGGCTTCAAACAAGTTCAAAGGATGGTG
METGluThrLeuGluGluLeuAspLeuCysLeuAspThrGlnLeuGluThrIleGlnThrTyrArgSerValSerGluMETAlaSerAsnLysPheLysArgMETLeu
AACCGGAGTGACACACCTCTCAGAGATGAGCAGATCAGGGAACCAAGTGTCTGAATACATTTCGAACACGTTCTTAGAACAGCAGACGATGTGGAAATCCA
AsnArgGluLeuThrHisLeuSerGluMETSerArgSerGlyAsnGlnValSerGluTyrIleSerAsnThrPheLeuAspLysGlnAsnAspValGluIleProA
TCTCCCACCCAGAAGGACAGGGAGAAGAAGAAGCAGCTCATGACCAGCTAGTGGAGTGAAGAAACTGATGCACAGCTCAAGCTCGAACAACAAGC
SerProThrGlnLysAspArgGluLysLysLysGlnLeuMETThrGlnIleSerGlyValLysLysLeuMETHisSerSerSerLeuAsnAsnThrSer
ATCTCACGCTTTGAGTCAACACGGAAATGAGGATCATCTAGCCAAGGAGCTGGAAGACCTGAACAAATGGGCCTTAACATCTTCAACGTGCTGGTACTCC
IleSerArgPheGluSerThrArgAsnGluAspHisLeuAlaLysGluLeuAspLeuAsnLysTrpGlyLeuAsnIlePheAsnValAlaGlyTyrSer
CATAATCGGCCCCTCACATGCATCATGTACGCCATTTTCCAGGAAAGAGACCTTCTAAAATCTCCGACACCTTCGTAACCTACTACATGATGACT
HisAsnArgProLeuThrCysIleMETTyrAlaIlePheGlnGluArgAspLeuLeuLysThrPheLysIleSerSerAspThrPheValThrTyrMETMETThr
TTAGAAGACCATTACCATTCTGATGTGGCTATCACAACAGCCTGCTCAAACGCAGTTCTCCTCTCTTACGCCAGCACTGGATGCT
LeuGluAspHisTyrHisSerAspValAlaTyrHisAsnSerLeuHisAlaAlaGlnSerThrHisValLeuLeuSerThrProAlaLeuAspAla
GTCTTCACAGACCTGGAAATCCTGGCTGCCATTTTGCAGCTGCCATCCATGATGTTGATCATCCTGGAGTCTCCAATCAGTTTCTCATCAATACAAATTCCGAA
ValPheThrAspLeuGluIleLeuAlaAlaIlePheAlaAlaIleHisAspValAspHisProGlyValSerAsnGlnPheLeuIleAsnThrAsnSerGlu
CTTGCTTTGATGTATAATGACCGAATCTGTCTGGAAAAACATCACCTCGCTGGATTCAAGCTCCTCAAGAGGAACATTGCGACATCTTTCAGAATCTTACC
LeuAlaLeuMETTyrAsnAspArgSerValLeuGluAsnHisHisLeuAlaValGlyPheLysLeuGlnGluGluLeuGlnIleCysAspIlePheGlnAsnLeuThr
AAGAAGCAACGCCAGACACTCAGGAAAATGTGATTGACAACTGGTTAGCAACTGATATGTCCAAGCACATGAGCCTCCTGGCTGACCTTAAAACGATGTAGAA
LysLysGlnArgGlnThrLeuArgLysMETValIleAspMETValLeuAlaThrAspMETSerLysHisMETSerLeuLeuAlaAspLeuLysThrMETValGlu

FIG. 3A

```
ACCAAAAAGGTGACGAGCTCCGGTGTTCTCCTCCTGGACAACTATACTGACCGGATACAGTTCTTCGCAACATGTGTACATTGTGCAGACCTGAGCAACCCTACC
ThrLysValThrSerSerGlyValLeuLeuLeuAspAsnTyrThrAspArgIleGlnValLeuArgAsnMETValHisCysAlaAspLeuSerAsnProThr

AAGTCCTTGGAGTTGTATCGGCAATGACTGATCGCATCATGGAGGAGTTTTCCAACAGGGAGAGAGAACGGAGAGGGAATGGAGATTAGCCCAATGTGT
LysSerLeuGluLeuTyrArgGlnTrpThrAspArgIleMETGluGluPheSerAsnArgGluArgGluArgGlyMETGluIleSerProMETCys

GATAAACACAGCTTCTGTGGAAAAGTCCCAGGTTGGTTTCATTGACTACATTGTCCATCCATTGTGGGAGACCTGGGCAGACCTGGTTCAGCCTGATGCTCAA
AspLysHisThrAlaSerValGluLysSerGlnValGlyPheIleAspTyrIleValHisProLeuTrpGluTrpAlaAspLeuValGlnProAspAlaGln

GACATTTGGACACACTAGAAGATAACAGGAACTGGTACCAGAGTATGATTCCCAGAGCCCCCTCCACCACTGACGAGAGGAGCAGGGACTGCCAAGGCCTT
AspIleTrpThrHisxxxArgAsnArgAsnTrpTyrGlnSerMETIleProSerProProLeuAspSerArgArgAspCysGlnGlyLeu ATGGAGAAGTTTCAGTTGGAACTGGAGCCCTTCAGTCTGAAGAAGACCGGAAAAGGAGGAGAAGGCCCAACTATTTCAGCAGCACAAAGACACTTTGT
METGluLysPheGlnLeuGluLeuGluLysThrLeuGluGluAspProGluLysGlyLeuGlyGluGlyProAsnTyrPheSerSerThrLysThrLeuCys GTGATCGATCCAGAGAACAGGGATTCTCTGGAAGAGAACTGACATAGACATTGCCACAGAAGACAGTTCTGATCGACACATAATCTCCCTCTGTGTGGAGGTGA
ValIleAspProGluAsnArgAspSerLeuGluGluThrAspIleAspIleAlaThrGluAspLysSerLeuIleAspThr ACATTCTATCCTTGACGAGCATGCCAGCTGAGTGGTAGGGCCCCACCTGAGCTAGGGCCCAAAACAAAGGCCACCTGGCTTTGCAGTTACTTGAGTTT GGAGCCAGAATGCAAGGCCGTGAAGCAAATAGCAGTTCCGTGCCTGCCTTGGCGAGACCCGCAGCTGTAGTAGAAGCCAGTTCCCAGCA CAGCTAAATGGCTTGAAAACAGAGGACAGAAAGCTGAGAGATTGCTCTGCAATAGGTGTTGAGGGGCTGTCCCGACAGGTGACTGAACTCACTAACAACTTCATC TATAAATCTCACCCATCCTGTTCTGCCAACCTGTGCCTTTTTGTAAAATGTTTCGTGTCTTTGAAATGCCTGTTGAATATCTAGAGTTTAGTACCTCCT TCTACAAACTTTTTTGAGTCTTTCTGGGAAAAAAAAAAAA                                                                2171
```

CTGCTGAAGAAATTCCGCATCCCTGTGGACACGATGGTGACATACATGCTGACGCTGGAGGATCACTACCACCGCTGAGTGGCCTACCATAACAGCCTGCAC
LeuLeuLysLysPheArgIleProValAspThrMETValThrTyrMETLeuThrLeuGluAspHisTyrHisAlaAspValAlaTyrHisAsnSerLeuHis

GCAGCTGACGTGCTGCAGTCCACCCACTGCTGGCCACGCCTTGGCCAACCTTAAGGAATGCAGTGTTCACGGACCTGGAGATTCTCGCCGCCCTCTTC
AlaAlaAspValLeuGlnSerThrHisValLeuLeuAlaThrProTrpProThrLeuArgAsnAlaValPheThrAspLeuGluIleLeuAlaAlaLeuPhe

GCGGCTGCCATCCACGATGTGGATCACCCTGGGTCTCCAACCAGTTCCTCATCAACACCAGTTCCTCAACACCACCAATTCGGAGCTGGGCTCATGTACAACGATGAGTCGGTGCTC
AlaAlaAlaIleHisAspValAspHisProGlyValSerAsnGlnPheLeuIleAsnThrAsnSerGluLeuAlaLeuMETTyrAsnAspGluSerValLeu

GAGAATCACCACCTGGCCGTGGGCTTCAAGCTGCTGCAGGAGGACAACTGCGACATCTTCCAGAACCTGCTGACCCTCCTGGCTGACCTGAAGACCATGACCCTCCTGGCTGACCTGAAGACCATGTGGAGACCAAGAAAGTGACCAGTCAGGGTC
GluAsnHisHisLeuAlaValGlyPheLysLeuLeuGlnGluAspAsnCysAspIlePheGlnAsnLeuSerLysArgGlnArgGlnSerLysArgLysMET

GTCATCGACATGGTGCTGGCCACGACATGTCCAAGCACATGACCCTCCTGGCTGACCTGAAGACCATGGTGGAGACCAAGAAAGTGACCAGTCAGGGTC
ValIleAspMETValLeuAlaThrAspMETSerLysHisMETThrLeuLeuAlaAspLeuLysThrMETValGluThrLysLysValThrSerGlyVal

CTCCTGCTAGATAACTACTCCGACCGCATCCAGTTCCTCCGGAACATGGTGCACTGTCCGACCTCAGCAACCCACCAAGCCGCTGGAGCTGTACCGCCAG
LeuLeuAspAsnTyrSerAspArgIleGlnValLeuArgAsnMETValHisCysAlaAspLeuSerAsnProThrLysProLeuGluLeuTyrArgGln

TGGACAGACCGCATCATGGCCGAGTTCTTCCAGCAGGTGACCGAGAGCGCGGAGCGTGGCATGGAAATCAGCCCCATGTGTGACAAGCACACTGCTCCGTG
TrpThrAspArgIleMETAlaGluPhePheGlnGlnValThrGluSerAlaGluArgGlyMETGluIleSerProMETCysAspLysHisThrAlaSerVal

GAGAAGTCTCAGGTGGGTTTATTGACTACATTGTGCACCATTGTGGGACCTGGGCGACCTTGTCCACCAGATGCCCAGGAGATCTTGACACTTTG
GluLysSerGlnValGlyPheIleAspTyrIleValHisProLeuTrpGluTrpAlaAspLeuValHisProAspAlaGlnGluIleLeuAspThrLeu

FIG. 4B

GAGGACAACCGGGACTGGTACTACAGCGCCATCCGGCAGAGCCCATCTCCGCCACCCGAGGAGAGTCAAGGGGCCAGGCCACCACCCTGCTGACAAG
GluAspAsnArgAspTrpTyrTyrSerAlaIleArgGlnSerProSerProProGluGluSerLysGlyProGlyHisProProLeuProAspLys

TTCCAGTTTGAGCTGACGCTGGAGGAGGAGGAAGAAATATCAATGCCCAGATACCGTGCACAGAGGCATTGACTGAGCAGGATTGTCA
PheGlnPheGluLeuThrLeuGluGluGluGluGluIleIleSerMETAlaGlnIleProCysThrAlaGlnIleAlaLeuThrGluGlnGlyLeuSer

GGAGTCGAGGAAGCTCTGGATGCAACCATAGCCTGGGAGGCATCCCGGCCCAGGAGTCGTTGGAAGTTATGGCACAGGAAGCATCCTGGAGGCCGAGCTG
GlyValGluGluAlaLeuAspAlaThrIleAlaTrpGluAlaSerProAlaGlnGluSerLeuGluValMETAlaGlnGluAlaSerLeuGluAlaGluLeu

GAGGCAGTGTATTGACACAGCAGGACAGTCCACAGGCACACTGTGGCTCCGATGAGTTCTCGTCCCGGAGGAATTCGTGTTGCTGTAAGCCAC
GluAlaValTyrLeuThrGlnGlnAlaGlnSerThrGlySerAlaProValAlaProAspGluPheSerSerArgGluPheValValAlaValSerHis

AGCAGCCCCTCTGCCTCTTCAAAGCCCCCTCTGCTTCTCCCTGCTTGGAGGACCCTGTCTGTTTCAGAGACATGCCCGGCTCCCGGGCTCCCCTCCACGGC
SerSerProSerAlaLeuAlaLeuGlnSerProLeuLeuProAlaTrpArgThrLeuSerValSerGluHisAlaArgProProGlyProProLeuHisGly

GGCCAGGTGAGGCCCAACAGAGCCACCAGGCTGCCAAGAGGGCTTGCAGTGCCTGCCCAGGACATTTGGGAGGACACATCCCAGCTCCTGG
GlyArgGlyGlyProThrArgAlaProGlyCysGlnGluGlyLeuGlnCysLeuArgArgAspIleTrpGlyGlyHisIleArgThrProSerSerTrp

TGGCGGGGGTCAGGTGAGACCTACCTGATCCCCAGACCCTGTCCCCTCACTCCCCTGCTCCCCCGACCACCTCCTCCT
TrpArgGlyValArgTrpArgProTyrLeuIleProArgProLeuLeuProArgProLeuThrProProLeuProArgProProProPro

CTGCCTCAAAGACTCTTGTCCTCTTGTCCGGGCCCAAGCTT
LeuProGlnArgLeuLeuSerSerCysProArgProGlnAla

FIG. 4C

```
JC99       AAGCTTGCGGCCCGCATTGGGTACCGCGTGCCAGCAGGCAGTGGCCCTAGCCTTCCGCCT
 60   ATGCCCTCCCTCCAAGAGGTGGACTGCGGCTCCCCCAGCAGCTCCGAGGAGGAGGGGTGCCAGGGTCCCGGGGG
  1   METProSerLeuGlnGluValAspCysGlySerProSerSerSerGluGluGluGlyValProGlySerArgGly

AGCCCAGCGACCTCACCCCACCTGGGCCCGCGACCTCTGCTTCGGTCCATGAGCGGCCCTTCTGCTCCCTA
      SerProAlaThrSerProHisLeuGlyArgArgArgProLeuLeuArgSerMETSerAlaAlaPheCysSerLeu

CTGGCACCGGAGCGGCAGGTGGGCCCGGGCTGCGGCAGCACTGATGCAGGACCGACACAGCCGGGCCAGCTG
      LeuAlaProGluArgGlnValGlyArgAlaAlaAlaAlaAlaLeuMETGlnAspArgHisThrAlaAlaGlyGlnLeu

GTGCAGGACCTACTGACCCAGGTGCGGGATGGGCCCCAGGAGCTCCGAGGGCATCCGTCAGGCGCTGAGC
      ValGlnAspLeuLeuThrGlnValArgAspGlyProGlnGluLeuGluGlyIleArgGlnAlaLeuSer

CGGGCCCGGGCCATGCTGAGTGCGGAGCTGGGCCCTGAGAAGCTCGTCTGCCTAAGAGCTGAACATGTCCTG
      ArgAlaArgAlaMETLeuSerAlaGluLeuGlyProGluLysLeuValSerProLysArgLeuHisValLeu

GAGAAGTCATTGCATTGCTCTGTGCTCAAGCCCTCCCGGCCCATCCTGGCCAGCCCGCCGGCGCGGCTTGCC
      GluLysSerLeuHisCysSerValLeuLysProLeuLeuArgProIleLeuAlaAlaArgLeuArgArgLeuAla

GCAGACGGCTCCCTGGGCCGCCTAGCTGAGGGCCTTCGCAGGCCCCCAGGGCCCGGAGCCTTCGGGTCC
      AlaAspGlySerLeuGlyArgLeuAlaGluAlaArgAlaGlnGlyProGlyAlaPheGlySer
```

FIG. 5A

CACCTGAGCCTGCCCTCCCCAGTAGAGTGGAGCAAGTGCCCAGAAGCTGCTGCAGCTCGTCCGCCACCTACTCA
HisLeuSerLeuProSerProValGluLeuGluGlnLysLeuGlnLeuLeuValArgThrTyrSer

CCCAGCGCCAGGTCAAGCGGCTCCTGCAGGCCCTGCTCTACATGGCCCTGAGGACCCAGGAAGGGGAG
ProSerAlaGlnValLysArgLeuLeuGlnAlaCysLysLeuLeuTyrMETAlaLeuArgThrGlnGluGlyGlu

GGCTCGGGTGCCGACGGGTTCCTGCCTCTGCTGAGCCTCGTCTTGGCCCACTGTGACCTTCCTGAGCTGCTG
GlySerGlyAlaAspGlyPheLeuProLeuLeuSerLeuValLeuAlaHisCysAspLeuProGluLeuLeu

GAGGCCGAGTACATGTCGGAGCTGCTGGAGCCCAGCTGCTTACTGGAGAGGGTGGCTACTACCTGACCAGCCTC
GluAlaGluTyrMETSerGluLeuLeuGluProSerLeuLeuThrGlyGluGlyGlyTyrTyrLeuThrSerLeu

TCTGCCAGCCTGGCCCTGCTGAGTGGGCTCCAGGCCCACACCCTCCCACTGAGCCCCGTGCAGGAGCTACGG
SerAlaSerLeuAlaLeuLeuSerGlyLeuGlnAlaHisThrLeuProLeuSerProValGlnGluLeuArg

CGCTCCCTCAGCCTCTGGGAGCAGCGCCTGCCACCACTGCTTCCAGCACCTCCTCCGAGTAGCCTAT
ArgSerLeuSerLeuTrpGluGlnArgArgLeuProAlaThrHisCysPheGlnHisLeuLeuArgValAlaTyr

CAGGATCCCAGCAGTGGCTGCACCTCCAAGACCCTGGCCGTGCCCCCAGAGACCCTCGATTGCCACCCTGAACCAG
GlnAspProSerSerGlyCysThrSerLysThrLeuAlaValProProGluAlaSerIleAlaThrLeuAsnGln

CTCTGTGCCACCAAGTTCCGAGTGACCCAGCCCAACACTTTTGGCCTTCTCTGTACAAGGAGCAGGGCTACCAC
LeuCysAlaThrLysPheArgValThrGlnProAsnThrPheGlyLeuPheLeuTyrLysGluGlnGlyTyrHis

CGCCTGCCCCCTGGGCCCCTGCCCACCAGGCTGCCACCACTGGCTACCTCGTCTACCCGGGCAGAGTGGCCTG
ArgLeuProProGlyProLeuProThrGlyCysProProLeuAlaThrSerSerThrAlaGlyGlnSerGlyLeu

AGACCCAGGGGGGCTGTGACAGAGGAGGGGCAGTGGGCAGTCAGAGGCAAGAAGCAGAGGGGAGGAGCAAGGGT
ArgProArgGlyLeu

GCCAGGGAGATGGGGATGCTGGGGTCAAAGCCAGCCCCCAGGGACATTCGGAACAGTCTGAGACAACTGCTGAAG

GGGGCCAGGGTCAAGCCCAGGAAGCCCTGCTCAGCCAGGGAACCAGAGGCAGAGGGAAGCCGGGCAGCAGAGG

AGTAGCTTGAAGTGGCCAGAAGGGTCATTCGGGGGAGACCCTGAGCCCTGCTGAGAAATCCTTTTAGCGCCAG

CAAGCCCCACCCAGGGCCCTGTCCTGTCTGCCACCACCTTTGTCTGATACTTGTTTCCAGGGAAGCTGGGGGA

ACTGCCACATCTGAGGAACTGGAATAAAGATGAGGGCCTTCGGGGGCCAATGCGGCCGCGGGCCTTTTGGC

CAGCTCGAATTC

30  GCGGCCGCGGGCCGGCAGCGGGCTGAGCGAC

1   ATGAGCATTTCTACTTCCTCCTCCGACTCGCTGGAGTTCGACCGGAGCATGCCTCTGTTGGCTACGAGGCGAC
    METSerIleSerThrSerSerSerAspSerLeuGluPheAspArgSerMETProLeuPheGlyTyrGluAlaAsp

ACCAACAGCAGCCTGGAGGACTACGAGGGGAAAGTGACCAAGAGACCATGGCGCCCCCATCAAGTCCAAAAAG
    ThrAsnSerSerLeuGluAspTyrGluGlyLysValThrLysArgProTrpArgProProIleLysSerLysLys

AAAAGGAGCAGCTCCTTCGTGCTGCCCAAGCTCGTCAAGTCCCAGCTCCAAGAAGTGAGCGGGGTGTTCAGCTCC
    LysArgSerSerSerPheValLeuProLysLeuValLysSerGlnLeuGlnLysValSerGlyValPheSerSer

TTCATGACCCCGGAGAAGCGGATGGTCCGCAGGATCGCCGAGCTTCCCGGACAAATGCACCTACTTCGGGTGC
    PheMETThrProGluLysArgMETValArgArgIleAlaGluLeuProGlyGlnMETHisLeuLeuArgValCys

TTAGTGCAGGACTACGTGAGCTTCCTGAGGAACAAGGAGTGCCACGTGTCCAGCACCGACATGCTGCAGACC
    LeuValGlnAspTyrValSerPheLeuArgAsnLysGluCysHisValSerSerThrAspMETLeuGlnThr

ATCCGGCAGTTCATGACCCAGTCAAGAACTATTTGTCTCAGAGCTCGGAGCTGGACCCCCATCGAGTCGCTG
    IleArgGlnPheMETThrGlnSerArgThrIleCysLeuSerGlnSerSerGluLeuAspProIleGluSerLeu

ATCCCTGAAGACCAAATAGATGTGGTGCTGGAAAAAGCCATGCACAAGTGCATCTTGAAGCCCCTCAAGGGGCAC
    IleProGluAspGlnIleAspValValLeuGluLysAlaMETHisLysCysIleLeuLysProLeuLysGlyHis

FIG. 6A

```
GTGGAGGCCATGCTGAAGGACTTTCACATGGCCGATGGCTCATGGAAGCAACTCAAGGAGAACCTGCAGCTTGTG
ValGluAlaMETLeuLysAspPheHisMETAlaAspGlySerTrpLysGlnLeuLysGluAsnLeuGlnLeuVal

CGGCAGAGGAATCCGCAGGAGCTGGGGGTCTTCGCCCCCGACCCCTGATTTTGTGGATGTGGAGAAAATCAAAGTC
ArgGlnArgAsnProGlnGluLeuGlyValPheAlaProThrProAspPheValAspValGluLysIleLysVal

AAGTTCATGACCATGCAGAAGATGTATTCGCCGGAAAAGAAGGTCATGCTGCTGCGGGTCTGCAAGCTCATT
LysPheMETThrMETGlnLysMETTyrSerProGluLysLysValMETLeuLeuArgValCysLysLeuIle

TACACGGTCATGGAGAACAACTCAGGGAGGATGTATGGCGTGATGACTTCTTGCCAGTCCTGACCTATGTCATA
TyrThrValMETGluAsnAsnSerGlyArgMETTyrGlyAlaAspPheLeuProValLeuThrTyrValIle

GCCCAGTGTGACATGCTTGAATTGGACACTGAAATCGAGTACATGATGGAGCTCCTAGACCCATGCTGTTACAT
AlaGlnCysAspMETLeuGluLeuAspThrGluIleGluTyrMETMETGluLeuLeuAspProSerLeuLeuHis

GGAGAAGGAGGCTATTACTTGACAAGCGCATATGGAGCACTTTCTCTGATAAAGAATTCCAAGAAGAACAAGCA
GlyGluGlyGlyTyrTyrLeuThrSerAlaTyrGlyAlaLeuSerLeuIleLysAsnPheGlnGluGlnAla

GCCGCGACTGCTCAGCTCAGAAACCAGAGACACCCTGAGGCAGTGGCACAAACGGAGAACCACCAACCGGACCATC
AlaArgLeuLeuSerGluThrArgAspThrLeuArgGlnTrpHisLysArgArgThrThrAsnArgThrIle
```

FIG. 6B

CCCTCTGTGGACGACTTCCAGAATTACCTCCGAGTTGCATTTCAGGAGGTCAACAGTGGTTGCACAGGAAAGACC
ProSerValAspAspPheGlnAsnTyrLeuArgValAlaPheGlnGluValAsnSerGlyCysThrGlyLysThr

CTCCTTGTGAGACCTTACATCACCACTGAGGATGTGTCAGATCTGCGCTGAGAAGTTCAAGGTGGGGACCCT
LeuLeuValArgProTyrIleThrThrGluAspValCysGlnIleCysAlaGluLysPheLysValGlyAspPro

GAGGAGTACAGCCTCTTTCTCTTCGTTGACGAGACATGGCAGCAGCTGGCAGAGAACACTTACCCTCAAAAAATC
GluGluTyrSerLeuPheLeuPheValAspGluThrTrpGlnGlnLeuAlaGluAsnThrTyrProGlnLysIle

AAGGCGGAGCTGCACAGCCGACCACAGCCCCACATCTTCCACTTTGTCTACAAACGCATCAAGAACGATCCTAT
LysAlaGluLeuHisSerArgProGlnProHisIlePheHisPheValTyrLysArgIleLysAsnAspProTyr

GGCATCATTTCCAGAACGGGGAAGAAGAAGACCTCCACCACCTCCTAGAAGACAGGCGGGACTTCCCAGTGGTCATC
GlyIleIlePheGlnAsnGlyGluGluAspLeuAspLeuThrSer                                474

CAAAGGGGAGCTGGAAGCCTTGCCTTCCCGCTTCTACATGCTTGAGCTTGAAAAGCAGTCACCTCCTCGGGGACC

CCTCAGTGTAGTGACTAAGCCATCCACAGGCCAACTCGGCCAAGGGCAACTTTAGCCACGCCAAGGTAGCTGAGGT

TTGTGAAACAGTAGGATTCTCTTTTGGCAATGGAGAATTGCATCTGATGGTTCAAGTGTCCTGAGATTGTTTGCT

ACCTACCCCCAGTCAGGTTCTAGGTTGGCTTACAGGTATGTATATGTGCAGAAGAAACACTTAAGATACAAGTTC

TTTGAATTCAACAGCAGATGCTTGCGATGCAGTGCGTCAGGTGATTCTCACTCCTGTGGATGGCTTCATCCCTG    1824

```
   1 GGCCGCATTGCCGACCCGGCCCGTAGTGTGGAAGCAGCTTCAGCTCAAAGATTAGAACGACTCCGAAAGAGAGA
   1 GlyArgIleAlaAspProAlaArgSerValGluAlaAlaSerAlaGlnArgLeuGluArgLeuArgLysGluArg

CAAAACCAGATCAAATGCAAAAAATATTCAGTGGAAAGAAAGAAATTCTAAGCAATCAGCCCAGGAGTTAAAGTCA
     GlnAsnGlnIleLysCysLysAsnIleGlnTrpLysGluArgAsnSerLysGlnSerAlaGlnGluLeuLysSer

CTGTTTGAAAAAAAATCTCAAAGAGAAGCCTCCAATTTCTGGGAAGCAGTCAGTCGATATTATCTGTACGCCTAGAA
     LeuPheGluLysLysSerLeuLysGluLysProIleSerGlyLysGlnSerIleLeuSerValArgLeuGlu

CAGTGCCCTCTGCAGCTGAATAACCCTTTTAACGAGTATTCCAAATTTGATGGCAAGGGTCATGTAGGTACAACA
     GlnCysProLeuGlnLeuAsnAsnProPheAsnGluTyrSerLysPheAspGlyLysGlyHisValGlyThrThr

GCAACCAAGAAGATCGATGTCTACCTCCCCTCTGCCTCGAGCCAGGACAGACTGCTGCCAATGACCGTGGTGACA
     AlaThrLysLysIleAspValTyrLeuProLeuHisSerSerGlnAspArgLeuLeuProMETThrValValThr

ATGGCCAGCGCCAGGGTGCAGGATCTGGGCTCATCTGCTGGCAGTATACAAGCGAAGGACGGGAGCCGAAG
     METAlaSerAlaArgValGlnAspLeuIleGlyLeuIleCysTrpGlnTyrThrSerGluGlyArgGluProLys
```

CTCAATGACAATGTCAGTGCCTACTGCCTGCATATTGCTGAGGATGATGGGGAGGTGGACACCGATTTCCCCCG
LeuAsnAspAsnValSerAlaTyrCysLeuHisIleAlaGluAspAspGlyGluValAspThrAspPheProPro

CTGGATTCCAATGAGCCCATTCATAAGTTTGGCTTCAGTACTTTGGCCCTGGTTGAAAAGTACTCATCTCCTGT
LeuAspSerAsnGluProIleHisLysPheGlyPheSerThrLeuAlaLeuValGluLysTyrSerSerProGly

CTGACATCCAAAGAGTCACTCTTTGTTCGAATAAATGCTGCTCATGGATTCTCCCTTATTCAGGTGGACAACACA
LeuThrSerLysGluSerLeuPheValArgIleAsnAlaAlaHisGlyPheSerLeuIleGlnValAspAsnThr

AAGGTTACCATGAAGGAAATCTTACTGAAGGCAGTGAAGCGAAGAAAAGGATCCCAGAAAGTTTCAGGCCCTCAG
LysValThrMETLysGluIleLeuLeuLysAlaValLysArgArgLysGlySerGlnLysValSerGlyProGln

TACCGCCTGGAGAAGCAGAGCCAGCCCAATGTCGCCGTTGACCTGGACAGCACTTTGGAGAGCCAGAGGCATGG
TyrArgLeuGluLysGlnSerGlnProAsnValAlaValAspLeuAspSerThrLeuGluSerGlnSerAlaTrp

GAGTTCTGCCTGGTCCGCGAGAACAGTTCAAGGGCAGACGGGTTTTTGAGGAGGATTCGCAAATTGACATAGCC
GluPheCysLeuValArgGluAsnSerSerArgAlaAspGlyValPheGluGluAspSerGlnIleAspIleAla

FIG. 7B

```
ACAGTACAGGATATGCTTAGCAGCCACCATTACAAGTCATTCAAAGTCAGCATGATCCACAGACTGCGATTCACA
ThrValGlnAspMETLeuSerSerHisHisTyrLysSerPheLysValSerMETIleHisArgLeuArgPheThr

ACCGACGTACAGCTAGGTATCTCTGGAGACAAAGTAGAGAGATAGACCCTGTTACGAATCAGAAAGCCAGCACTAAG
ThrAspValGlnLeuGlyIleSerGlyAspLysValGluIleAspProValThrAsnGlnLysAlaSerThrLys

TTTTGGATTAAGCAGAAACCCATCTCAATCGATTCCGACCCTGCTCTGTGCCTTGTGACCTTGCTGAAGAGAAAGC
PheTrpIleLysGlnLysProIleSerIleAspSerAspLeuLeuCysAlaCysAspLeuAlaGluGluLysSer

CCCAGTCACGGCAATATTTAAACTCACGTATCTAAGCAATCACGACTATAAACACCTCTACTTTGAATCGGACGCT
ProSerHisAlaIlePheLysLeuThrTyrLeuSerAsnHisAspTyrLysHisLeuTyrPheGluSerAspAla

GCTACCGTCAATGAAATTGTGCTCAAGGTTAACTACATCCTGGAATCGCGAGCTAGCACTGCCCGGGCTGACTAC
AlaThrValAsnGluIleValLeuLysValAsnTyrIleLeuGluSerArgAlaSerThrAlaArgAlaAspTyr

TTTGCTCAAAAAAAAAGCGGGCCGC        1301
PheAlaGlnLysLysSerGlyArg          434
```

FIG. 7C

METHODS FOR IDENTIFYING MODULATORS OF GENE EXPRESSION

CROSS-REFERENCE TO RELATED APPLICATION

This application is a divisional application of U.S. Ser. No. 07/511,715 filed Apr. 20, 1990 now U.S. Pat. No. 6,080,540.

This invention was made with Government support under Grant number CA39829 awarded by the National Cancer Institute division of the National Institutes of Health. The Government may own certain rights in this invention.

BACKGROUND OF THE INVENTION

Presently, there are several methods available for cloning mammalian genes. The standard approach to cloning mammalian genes requires obtaining purified protein, determining a partial amino acid sequence of the purified protein, using the partial amino acid sequence to produce degenerate oligonucleotide probes, and screening cDNA libraries with these probes in order to obtain cDNA encoding the protein. This method is time consuming and, because of the degeneracy of the probes used, may identify sequences other than those encoding the protein(s) of interest. Many mammalian genes have been cloned this way, including the cGMP phosphodiesterase expressed in retina (Ovchinnikov, Y-A. et al., *FEB* 223: 169 (1987)).

A second approach to cloning genes encoding a protein of interest is to use a known gene as a probe to find homologs. This approach is particularly useful when members of a gene family or families are sufficiently homologous. It is reasonable to expect that members of a given gene family can be so cloned once one member of the family has been cloned. The *D. melanogaster* dunce phosphodiesterase gene was used, for example to clone rat homologs. (Davis, R. L. et al.; *Proc. Natl. Acad. Sci. USA* 86: 3604 (1989); Swinnen, J. V. et al., *Proc. Natl. Acad. Sci. USA* 86: 5325 (1989)). Although members of one family of phosphodiesterase genes might be cloned once a member of that family has been cloned, it is unclear whether the nucleotide sequences of genes belonging to different phosphodiesterase gene families exhibit sufficient homology to use probes derived from one family to identify members of another family.

It would be useful to have a method which could be used to clone genes which does not have the limitations of presently available techniques.

SUMMARY OF THE INVENTION

The present invention relates to a method of cloning mammalian genes encoding proteins which can function in microorganisms, particularly yeast, and can modify, complement, or suppress a genetic defect associated with an identifiable phenotypic alteration or characteristic in the microorganism. It further relates to mammalian genes cloned by the present method, as well as to products encoded by such genes and antibodies which can bind the encoded proteins. More specifically, the present invention relates to a method of cloning mammalian genes which encode products which modify, complement or suppress a genetic defect in a biochemical pathway in which cAMP participates or in a biochemical pathway which is controlled, directly or indirectly, by a RAS protein, to products (RNA, proteins) encoded by the mammalian genes cloned in this manner and to antibodies which can bind the encoded proteins. As described herein, the present method has been used to identify novel mammalian genes which encode cAMP, phosphodiesterases and proteins which interact with RAS proteins. These genes, and others that can be derived by the claimed method, are part of this invention, as are the proteins which they encode.

The present invention further relates to a method of identifying agents which alter (i.e., reduce or stimulate) the activity of the protein products of such mammalian genes expressed in microorganisms, such as yeast. Identification of such agents can be carried out using two types of screening procedures: one based on biochemical assays of mammalian proteins of known enzymatic function and one based on phenotypic assays for proteins of unknown function. In the former case, if the encoded proteins are cAMP phosphodiesterases, pharmacological screens include the assay for agents which alter (i.e., reduce or stimulate) phosphodiesterase activity. In the latter case, if the encoded proteins interact with RAS proteins, pharmacological screens include the assay for agents which reduce or stimulate interactions with RAS proteins.

BRIEF DESCRIPTION OF THE DRAWINGS

FIG. 2 is a schematic representation of the yeast expression vectors used to clone mammalian cDNAs. In FIG. 2B, the stippled area indicates a portion of the ADH coding sequences.

FIG. 3 is the nucleotide sequence of DPD cDNA (top line) and its deduced amino acid sequence (bottom line). Nucleotide and amino acid coordinates are given in the left hand margin.

FIG. 4 is the nucleotide sequence and the deduced amino acid sequence of cDNA clone #44. Nucleotide and amino acid coordinates are given in the left hand margin.

FIG. 5 is the nucleotide sequence and the deduced amino acid sequence of cDNA clone #99. Nucleotide and amino acid coordinates are given in the left hand margin.

FIG. 6 is the nucleotide and the deduced amino acid sequence of cDNA clone #265. Nucleotide and amino acid coordinates are given in the left hand margin.

FIG. 7 is the nucleotide sequence and the deduced amino acid sequence of cDNA clone #310. Nucleotide and amino acid coordinates are given in the left hand margin.

DETAILED DESCRIPTION OF THE INVENTION

Figure 1:
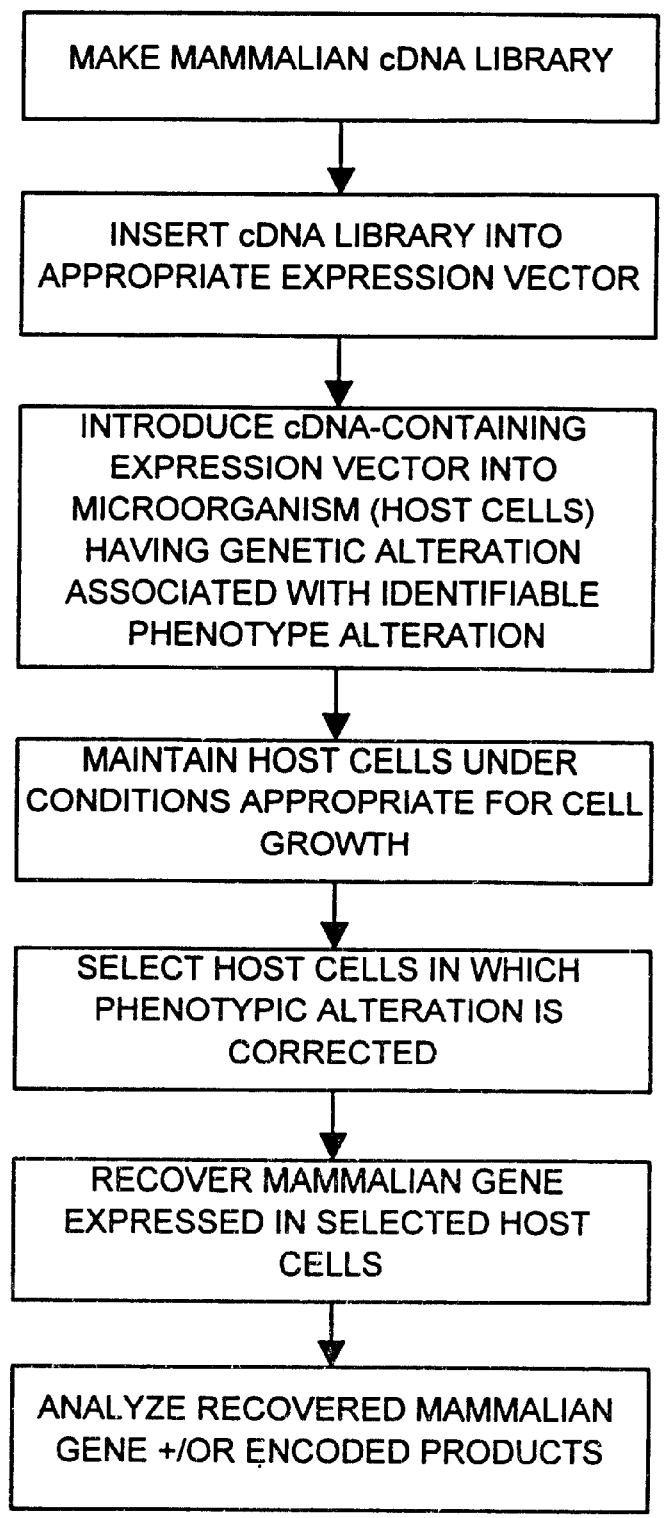
FIG. 1 is a flow diagram of the steps of the present method of cloning a mammalian gene which encodes a product capable of correcting a genetic alteration in a microorganism which is associated with an identifiable phenotypic characteristic.

The present invention relates to a method of cloning a mammalian gene which, when expressed in a microorganism, can modify, complement or suppress, in the microorganism, a genetic alteration or defect which is associated with an identifiable phenotype. Cloning of a selected mammalian gene is carried out according to the present method by introducing the gene into a genetically altered microorganism which has an identifiable phenotypic alteration or characteristic associated with the genetic alteration; maintaining the genetically altered microorganism in which the gene is present under conditions appropriate for cell growth; and selecting cells in which the phenotypic alteration or characteristic is modified as a result of correction, complementation or suppression of the genetic alteration or defect by the introduced mammalian gene. The present invention further relates to mammalian genes cloned by the present method, products (e.g., RNA, proteins) encoded by such genes and antibodies specific for encoded proteins. In particular, the present invention relates to a method of cloning and isolating a selected mammalian gene which, when expressed in yeast having a genetic alteration or defect associated with an identifiable phenotypic characteristic or alteration, corrects, complements or supplements the genetic alteration and modifies or corrects the associated phenotypic characteristic.

Through use of the method described herein, mammalian genes capable of modifying phenotypic alterations in yeast associated with activation or attenuation of biochemical pathways in which cAMP participates or with biochemical pathways which interact with or are controlled by RAS proteins have been identified, cloned and characterized. As described herein, the subject method has been used to clone mammalian genes encoding cAMP phosphodiesterases or proteins which interact with a RAS protein. This has been accomplished using yeast cells in which there is a genetic alteration in the RAS2 gene and which, as a result, are heat shock sensitive. Additional mammalian genes having these same characteristics can be identified, cloned and characterized using the method described. In each case, an appropriately-selected genetically altered host cell (e.g., yeast) is used for expression of the selected mammalian gene, which generally is introduced as one component of a gene library. The genetic alteration in the host cell is selected in such a manner that it is associated with an identifiable phenotypic characteristic which is corrected upon expression of the mammalian gene. The genetic alteration can be a deletion of a gene or a portion of a gene, a change in nucleotide sequence or any other nucleotide manipulation which renders a gene unable to function normally. The genetic alteration is selected in such a manner that a gene of interest can be identified when it is expressed in the altered host cell.

The mammalian genes, when expressed in yeast containing a genetic defect in a biochemical pathway, can correct, complement or alter the genetic defect and correct the phenotypic alteration (i.e., produce a phenotype more like that of normal or unaltered yeast). Cells containing the mammalian gene to be cloned are identified on the basis of correction or suppression of the phenotypic characteristic. The correction or suppression need not be complete.

As described herein, it is now possible to identify inhibitors and activators of cAMP phosphodiesterases, which can be used therapeutically to control or regulate cAMP levels or activity. In addition, it is now possible to identify agents which inhibit or stimulate interaction of gene products with RAS proteins.

It is one of the objects of this invention to discover, isolate and characterize new genes encoding cAMP phosphodiesterases. It is a further object of this invention to describe methods for identifying chemical agents which inhibit or stimulate cAMP phosphodiesterases and can be used for therapeutic purposes. Both of these objectives can be achieved through use of methods, described herein, for cloning genes encoding cAMP phosphodiesterases and expressing the proteins that they encode in cells with little or no other cAMP phosphodiesterase activity. Typically, cells used for expressing the proteins to be analyzed for cAMP phosphodiesterase activity lack other cAMP phosphodiesterase activity. Extracts from such cells thus provide a means by which agents which alter cAMP phosphodiesterases can be identified and isolated.

It is one of the further objects of this invention to discover, isolate and characterize new genes encoding products that interact with RAS proteins. It is still a further object of this invention to describe methods for identifying agents which inhibit or stimulate the interaction of these new gene products with RAS. This is accomplished through use of methods described herein for cloning genes encoding proteins that interact with RAS, and expressing the encoded proteins in cells that have phenotypes which are sensitive to the activity of these proteins.

The following is a description of cAMP phosphodiesterases; pathways controlled by RAS proteins; use of the present method for identification of mammalian genes, exemplified by identification of genes encoding cAMP phosphodiesterases and genes encoding products which interact with RAS proteins; use of the method to screen for agents which inhibit or stimulate cAMP phosphodiesterases; screening for agents which inhibit or stimulate interaction of such proteins with RAS proteins; and uses of the invention.

cAMP Phosphodiesterases

Adenylyl cyclase is an ubiquitous enzyme which generates cyclic adenosine monophosphate (cAMP). cAMP is a universal "second messenger" in both eukaryotes and prokaryotes. In eukaryotes, cAMP exerts its profound effects on cellular physiology by stimulating a cAMP-dependent protein kinase (Robinson, G. A., et al., *In Cyclic AMP*, Academic Press (1971)). This kinase is composed of regulatory and catalytic subunits. The regulatory subunits combine with and inhibit the catalytic subunits. When the regulatory subunits bind cAMP, they release the catalytic subunits, which in turn phosphorylate proteins on serine and threonine residues. The genes encoding the catalytic and regulatory subunits have been cloned from yeast and mammals (Toda, T., et al., *Cell* 50: 277 (1987); Shoji, S., et el., *Biochemistry* 22: 3702 (1983); Showers, M. O. and Mauver, R. A., *J. Biol. Chem.* 261: 16288 (1986); Titani, K. et al., *Biochemistry* 23: 4193 (1984); Takio, K., et al., *Biochemistry* 23: 4200 (1984)).

In mammals, cAMP is generated by cells in response to hormones, growth factors, and neurotransmitters (Robison, G. A. et al., *Cyclic AMP*, Academic Press, New York and London (1971)). The concentration of cAMP in mammalian cells is determined not only by its rate of production by adenylyl cyclase, but also by its rate of degradation by enzymes called phosphodiesterases, or more specifically, cAMP phosphodiesterases.

A number of important physiological responses in humans are controlled by cAMP levels, including mental function, smooth muscle relaxation, strength of cardiac contractility, release of histamine and other immunoreactive molecules, lymphocyte proliferation and platelet aggregation (Robison, G. A. et al., *Cyclic AMP*, Academic Press, New York and London (1971)). Thus, the range of diseases which can potentially be affected by agents or pharmaceutical compounds which alter cAMP levels include inflammatory processes (e.g., arthritis and asthma), heart failure, smooth muscle cramps, high blood pressure, blood clotting, thrombosis, and mental disorders. One way to modulate cAMP levels in cells is through the modulation of cAMP phosphodiesterase activity.

Many drugs which raise cAMP levels in various tissues are in common use. These drugs are useful in treating heart failure, asthma, depression and thrombosis. Only a few of these drugs appear to work by inhibiting cAMP phosphodiesterases. The pharmaceutical industry has not been notably successful at finding such drugs, since effective drug screens have not been available. The reasons for this are set forth below.

Most tissues contain so many different isoforms of phosphodiesterases that drug screening based on inhibition of crude tissue extracts is unlikely to yield anything other than a broadly acting inhibitor of phosphodiesterases. Broadly acting inhibitors of cAMP phosphodiesterases, such as theophylline, have many deleterious side effects. A few inhibitors are known which have narrow specificity. Such inhibitors may have great potential utility because they can target phosphodiesterases in one or a few tissue and cell types and thus have a higher therapeutic index.

The yeast cAMP phosphodiesterase genes PDE1 and PDE2 were the first phosphodiesterase genes cloned (Sass, P., et al., *Proc. Natl. Acad. Sci. USA,* 83: 9303 (1986); Nikawa, J., et al., *Mol. Cell. Biol.,* 7: 3629 (1987)). Comparison of the amino acid sequence of the yeast phosphodiesterases to the amino acid sequences of other eukaryotic phosphodiesterases reveals only limited sequence homology. PDE2 has very slight sequence homology to the dunce phosphodiesterase of *D. melanogaster* and to two phosphodiesterases expressed in bovine heart and brain (Charbonneau, H., et. al., *Proc. Natl. Acad. Sci.,* 83: 9308 (1986)). PDE1 shares even less of this homology, but resembles to a greater extent a secreted form of phosphodiesterase found in *D. discoidem* (Nikawa, J., et al., *Mol. Cell. Biol.* 7: 3629 (1987)). Thus, there appear to be many diverse branches of cAMP phosphodiesterase genes in evolution.

Biochemical, serological and pharmacological studies strongly suggest the existence of multiple families of cAMP phosphodiesterases in mammals (Beavo, J. A. *Advances in Second Messenger and Phosphoprotein Research* Vol. 22 1 (1988)). Partial amino acid sequence data and recent nucleic acid sequence data confirm this (Charbonneau, H., et al., *Proc. Natl. Acad. Sci., USA* 83: 9308 (1986); Colicelli, J., et al., *Proc. Natl. Acad. Sci. USA* 86: 3566 (1989); Davis, R. L., et al., *Proc. Natl. Acad. Sci. USA* 86: 3604 (1989); Swinnen, J. V., et al., *Proc. Natl. Acad. Sci. USA* 86: 5325 (1989)).

The various known phosphodiesterases fall into several classes: (I) $Ca^{++}$/calmodulin dependent, (II) cGMP stimulated, (III) cGMP inhibited, (IV) high affinity cAMP, (V) cGMP and (VI) nonspecific phosphodiesterases. Each class may be made up of a family of related proteins. In some cases these related proteins may be encoded by separate genes and in other cases they may arise from alternative gene splicing. Generally, a tissue expresses multiple classes of phosphodiesterases, which, by their copurification and proteolytic degradation, render biochemical analysis exceedingly difficult. The analysis of this complexity is aided somewhat by the availability of a few pharmacological agents which discriminate between different classes of phosphodiesterases, and, recently, by serological reagents which can distinguish between families and sometimes between members of a family (Beavo, J. A. *Advances in Second Messenger and Phosphoprotein Research* Vol. 22: 1–38 (1988)).

The classification of mammalian phosphodiesterases may not be complete, however. New families and types of activities may yet be discovered. The great majority of the cAMP phosphodiesterase genes have not yet been cloned.

Pathways controlled by RAS proteins

The RAS genes were first discovered as the transforming principles of the Harvey and Kirsten murine sarcoma viruses (Ellis, R. W., et al., *Nature* 292: 506 (1981)). The cellular homologs of the oncogenes of Harvey and Kirsten murine sarcoma viruses (H-RAS and K-RAS) constitute two members of the RAS gene family (Shimizu, K et al., *Proc. Natl. Acad. Sci.* 80: 2112 (1983)). A third member is N-RAS (Shimizu, K. et al., *Proc. Natl. Acad. Sci.* 80: 2112 (1983)). These genes are known as oncogenes since point mutations in RAS can result in genes capable of transforming non-cancerous cells into cancerous cells (Tabin, C. J., et al., *Nature* 300: 143 (1982); Reddy, E. P., et al., *Nature* 300: 149 (1982); Taparowsky, E., et al., *Nature* 300: 762 (1982);). Many tumor cells contain RAS genes with such mutations (Capon, D. J., et al., *Nature* 302: 33 (1983); Capon, D. J., et al., *Nature* 304: 507 (1983); Shimizu, K. et al., *Nature* 304: 497 (1983); Taparowsky, E., et al., *Cell* 34: 581 (1983); Taparowsky, E., et al., *Nature* 300: 762 (1982); Barbacid, M., *Ann. Rev. Biochem.* 56: 779 (1987)).

Despite the importance of the RAS oncogenes to our understanding of cancer, the function of RAS genes in mammals is not known. The RAS proteins are small proteins (21,000 daltons in mammals) which bind GTP and GDP (Papageorge, A., et al., *J. Virol.* 44: 509 (1982)). The RAS proteins hydrolyze GTP slowly; specific cellular proteins can accelerate this process (McCrath, J. P., et al., *Nature* 310: 644 (1984); Trahey, M., et al., *Science* 238: 542 (1987)). RAS proteins bind to the inner surface of the plasma membrane (Willingham, M. C., et al., *Cell* 19: 1005 (1980)) and undergo a complex covalent modification at their carboxy termini (Hancock, J. F., et al., *Cell* 57: 1167 (1989)). The crystal structure of H-RAS is known (De Vos, A. M. et al., *Science* 239: 888 (1988)).

The yeast *Saccharomyces cerevisiae* contains two genes, RAS1 and RAS2, that have structural and functional homology with mammalian RAS oncogenes (Powers, S., et al., *Cell* 36: 607 (1984); Kataoka, T., et al., *Cell* 40: 19 (1985) Defeo-Jones, D. et al., *Sciene* 228: 179 (1985); Dhar, R., et al., *Nucl. Acids Res.* 12: 3611 (1984)). Both RAS1 and RAS2 have been cloned from yeast plasmid libraries and the complete nucleotide sequence of their coding regions has been determined (Powers, S., et al., *Cell* 36: 607 (1984); DeFeo-Jones, D., et al., *Nature* 306: 707 (1983)). The two genes encode proteins with nearly 90% identity to the first 80 amino acid positions of the mammalian RAS proteins, and nearly 50% identity to the next 80 amino acid positions. Yeast RAS1 and RAS2 proteins are more homologous to each other, with about 90% identity for the first 180 positions. After this, at nearly the same position that the mammalian RAS proteins begin to diverge from each other, the two yeast RAS proteins diverge radically. The yeast RAS proteins, like proteins encoded by the mammalian genes, terminate with the sequence cysAAX, where A is an aliphatic amino acid, and X is the terminal amino acid (Barbacid, M., *Ann., Rev. Biochem.* 56: 779 (1987)). Monoclonal antibody directed against mammalian RAS proteins immumoprecipitates RAS protein in yeast cells (Powers, S., et al., *Cell* 47: 413 (1986)). Thus, the yeast RAS proteins have the same overall structure and interrelationship as is found in the family of mammalian RAS proteins.

RAS genes have been detected in a wide variety of eukaryotic species, including *Schizosaccharomyces pombe, Dictyostelium discoidem* and *Drosophila melanogaster* (Fukui, Y., and Kaziro, Y., *EMBO* 4: 687 (1985); Reymond, C. D. et al., *Cell* 39: 141 (1984); Shilo, B-Z., and Weinberg, R. A., *Proc. Natl. Acad. Sci., USA* 78: 6789 (1981); Neuman- Silberberg, F., *Cell* 37: 1027 (1984)). The widespread distribution of RAS genes in evolution indicates that studies of RAS in simple eukaryotic organisms may elucidate the normal cellular functions of RAS in mammals.

Extensive genetic analyses of the RAS1 and RAS2 of *S. cerevisiae* have been performed. By constructing in vitro RAS genes disrupted by selectable biochemical markers and introducing these by gene replacement into the RAS chromosomal loci, it has been determined that neither RAS1 nor RAS2 is, by itself, an essential gene. However, doubly RAS deficient (ras1⁻ ras2⁻) spores of doubly heterozygous diploids are incapable of resuming vegetative growth. At least some RAS function is therefore required for viability in *S. cerevisiae* (Kataoka, T., et al., *Cell* 37: 437 (1984)). It has also been determined that RAS1 is located on chromosome XV, 7 cM from ADE2 and 63 cM from HIS3; and that RAS2 is located on chromosome XIV, 2 cM from MET4 (Kataoka, T., et al., *Cell* 37: 437 (1984)).

Mammalian RAS expressed in yeast can function to correct the phenotypic defects that otherwise would result from the loss of both RAS1 and RAS2.(Kataoka, T., et al., *Cell* 40: 19 (1985)). Conversely, yeast RAS are capable of functioning in vertebrate cells (De Feo-Jones, D., et al., *Science* 228: 179 (1985)). Thus, there has been sufficient conservation of structure between yeast and human RAS proteins to allow each to function in heterologous host cells.

The missense mutant, $RAS2^{val19}$, which encodes valine in place of glycine at the nineteenth amino acid position, has the same sort of mutation that is found in some oncogenic mutants of mammalian RAS genes (Tabin, C. J., et al., *Nature* 300: 143 (1982); Reddy, E. P., et al., *Nature* 300: 149 (1982); Taparowsky, E., et al., *Nature* 300: 762 (1982)). Diploid yeast cells that contain this mutation are incapable of sporulating efficiently, even when they contain wild-type RAS alleles (Kataoka, T., et al., *Cell* 37: 437 (1984)). When an activated form of the RAS2 gene (e.g., $RAS2^{val19}$) is present in haploid cells, yeast cells fail to synthesize glycogen, are unable to arrest in G1, die rapidly upon nutrient starvation, and are acutely sensitive to heat shock (Toda, T., et al., *Cell* 40: 27 (1985); Sass, P., et al. *Proc. Natl. Acad. Sci.* 83: 9303 (1986)).

*S. cerevisiae* strains containing $RAS2^{val19}$ have growth and biochemical properties strikingly similar to yeast carrying the IAC or bcyl⁻ mutations, which activate the cAMP pathway in yeast (Uno, I., et al., *J. Biol. Chem.* 257: 14110 (1981)). Yeast strains carrying the IAC mutation have elevated levels of adenylate cyclase activity. bcyl– cells lack the regulatory component of the cAMP dependent protein kinase (Uno, I. et al., *J. Biol. Chem.* 257: 14110 (1982); Toda, T., et al., *Mol. Cell. Biol* 7: 1371 (1987)). Yeast strains deficient in RAS function exhibit properties similar to adenylate cyclase-deficient yeast (Toda, T., et al., *Cell* 40: 27 (1985)). The bcyl⁻ mutation suppresses lethality in ras1⁻ ras2⁻ yeast. These results suggest that in the yeast *S. cerevisiae*, RAS proteins function in the cAMP signalling pathway.

Adenylyl cyclase has been shown to be controlled by RAS proteins (Toda, T., et al., *Cell* 40: 27 (1985)). RAS proteins, either from yeast or humans, can stimulate adenylyl cyclase up to fifty fold in in vitro biochemical assays. RAS proteins will stimulate adenylyl cyclase only when bound with GTP (Field, J., et al., *Mol. Cell. Biol.* 8: 2159 (1988)).

The phenotypes which are due to activation of RAS, including sensitivity to heat shock and starvation, are primarily the result of overexpression or uncontrolled activation of the cAMP effector pathway via adenylyl cyclase (Kataoka, T., et al., *Cell* 37: 437 (1984); Kataoka, T. et al., *Cell* 43: 493 (1985); Toda, T. et al., *Cell* 40: 27 (1985); Field, J., et al., *Mol. Cell. Biol.*, 8: 2159 (1988)). Two *S. cerevisiae* yeast genes, PDE1 and PDE2, which encode the low and high affinity cAMP phosphodiesterases, respectively, have been isolated (Sass, P., et al., *Proc. Natl. Acad. Sci.* 83: 9303 (1986); Nikawa, J., et al., *Mol. Cell. Biol.* 7: 3629 (1987)). These genes were cloned from yeast genomic libraries by their ability to suppress the heat shock sensitivity in yeast cells harboring an activated $RAS2^{val19}$ gene. Cells lacking the PDE genes (i.e., pde1⁻ pde2⁻ yeast) are heat shock sensitive, are deficient in glycogen accumulation, fail to grow on an acetate carbon source, and in general have defects due to activation of the cAMP signaling pathway (Nikawa, J., et al., *Mol. Cell. Biol.* 7: 3629 (1987)).

Genetic analysis clearly indicates that RAS proteins have other functions in *S. cerevisiae* besides stimulating adenylyl cyclase (Toda, T. et al., *Japan Sci Soc. Press. Tokyo/VNU Sci. Press*, pp. 253 (1987); Wigler, M. et al., *Cold Spring Harbor Symposium*, Vol. LIII 649 (1988); Michaeli, T., et al., *EMBO* 8: 3039 (1989)). The precise biochemical nature of these functions is unknown. Experiments with other systems, such as *S. pombe* and *Xenopus laevis* oocytes, indicate that RAS stimulation of adenylyl cyclase is not widespread in evolution (Birchmeier, C., et al., *Cell* 43: 615 (1985)). It is unlikely that RAS stimulates adenylyl cyclase in mammals (Beckner, S. K. et al., *Nature* 317: 71 (1985)).

Identification of Mammalian Genes, Exemplified by Genes Encoding cAMP Phosphodiesterases The present method can be used to clone a mammalian gene of interest which functions in a microorganism which is genetically altered or defective in a defined manner (an altered microorganism) to correct the genetic alteration or defect and, as a result, modifies an identifiable phenotypic alteration or characteristic associated with the genetic alteration or defect (produces a phenotype more like that of normal or unaltered yeast). Although use of the present method to clone and identify mammalian genes is described in detail in respect to cAMP phosphodiesterases and proteins which interact with RAS proteins, it can be used to clone and identify other mammalian genes which function in an appropriately-selected altered microorganism to correct, complement or supplement the genetic alteration and, as a result, correct the associated phenotypic alteration.

In its most general form, the method of the present invention is represented in FIG. 1 and can be described as follows: A cDNA library of mammalian mRNAs is produced, using known techniques. This library can be made by cloning double stranded cDNA into an expression vector. The cDNA can be prepared from a preexisting cDNA library, or it can be prepared by the reverse transcription of mRNA purified from a tissue or cell line of choice, using standard procedures (Watson, C. J. and Jackson, J. F. *In: DNA cloning, a practical approach*, IRL Press Oxford (1984)). This is described in greater detail in Example 1, in which cDNA was derived from rat brain mRNA and in Example 2, in which the cDNA was derived from a human glioblastoma cell line, U1188MG.

Figure 2A:
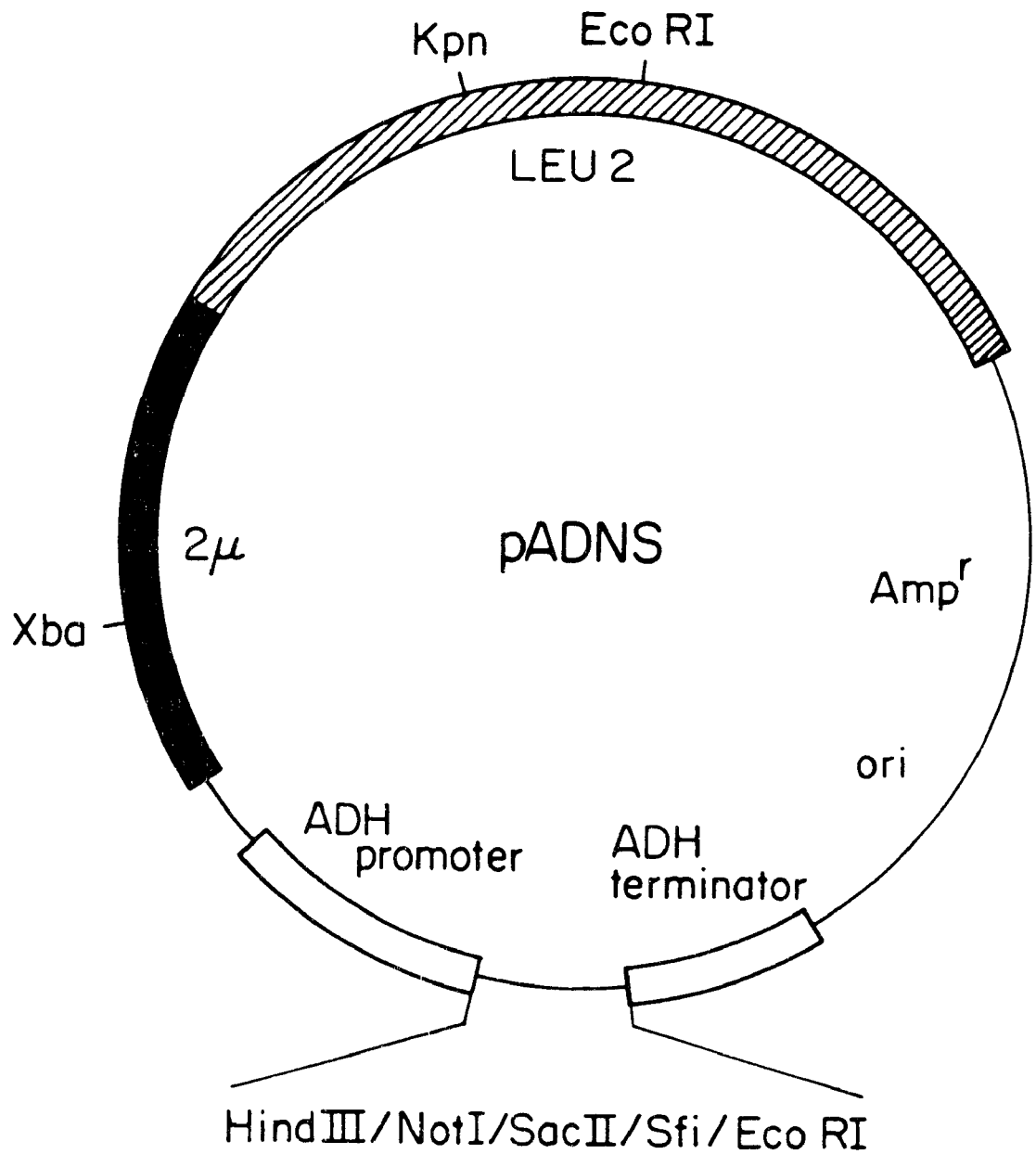
FIG. 2A is a schematic representation of yeast expression vector pADNS.

The cDNA obtained is cloned into an expression vector capable of expressing mammalian cDNA inserts as mRNA which can be translated into protein in a host cell of choice. Any expression vector, such as pADNS, into which the cDNA can be inserted and subsequently expressed as mRNA which is translated in an appropriate altered host cell (e.g., altered yeast) can be used. Vectors which have been used for this purpose are described; see FIG. 2A, which is a schematic representation of the expression vector TK161-R2V, whose use is described in Examples 1 and 2, and FIG. 2B, which is a schematic representation of the expression vector pADNS, whose use is described in Example 2. In general, an expression vector contains a transcriptional promoter specific for the host cell into which the vector is introduced For example, the vector used in Examples 1 and 2 contains promoters for expression in S. cerevisiae. The expressed mRNA may utilize the ATG of the cDNA insert as the "start" codon (e.g., the vector of FIG. 2A) or may express the cDNA product as a fusion protein (e.g., the vector of FIG. 2B).

The cDNA library (present as cDNA inserts in a selected expression vector) is introduced into a host cell of choice, which contains genetic alterations which cause the host cell to have an identifiable phenotypic alteration or abnormality associated with the genetic alteration. The host cell may be a eukaryotic microorganism, such as the yeast S. cerevisiae. Known methods, such as lithium acetate-induced transformation, are used to introduce the cDNA-containing expression vector. The genetic alterations may lead to defects in the metabolic pathways controlled by the RAS proteins and the associated readily discernible phenotype may be sensitivity to heat shock or nitrogen starvation, failure to synthesize normal amounts of glycogen, failure to grow on certain carbon sources, failure to sporulate, failure to mate, or other properties associated with defects in the pathways controlled by RAS proteins. For example, as described in Examples 1 and 2, the genetic alteration can be the presence of the $RAS2^{val19}$ gene. Yeast containing such an alteration exhibit heat shock sensitivity, which, as described in Examples 1 and 2, can be overcome by expression of mammalian genes. Other genetic alterations can be chosen, such as disruptions of the PDE1 and PDE2 genes in S. cerevisiae or disruptions of, or the presence of an activated allele of, ras1 in S. pombe. Different genetic alterations in the host cell may be correctable by different subsets of mammalian cDNA genes.

After introduction of the cDNA insert-containing expression vector, host cells are maintained under conditions appropriate for host cell growth. Those host cells which have been corrected for their phenotypic alteration are selected and the mammalian gene which they express is recovered (e.g., by transformation of E. coli with DNA isolated from the host cell). The mammalian gene is isolated and can be sequenced and used for further analysis in a variety of ways. For example, the encoded protein can be identified and expressed in cultured cells for use in further processes.

Figure 4A:
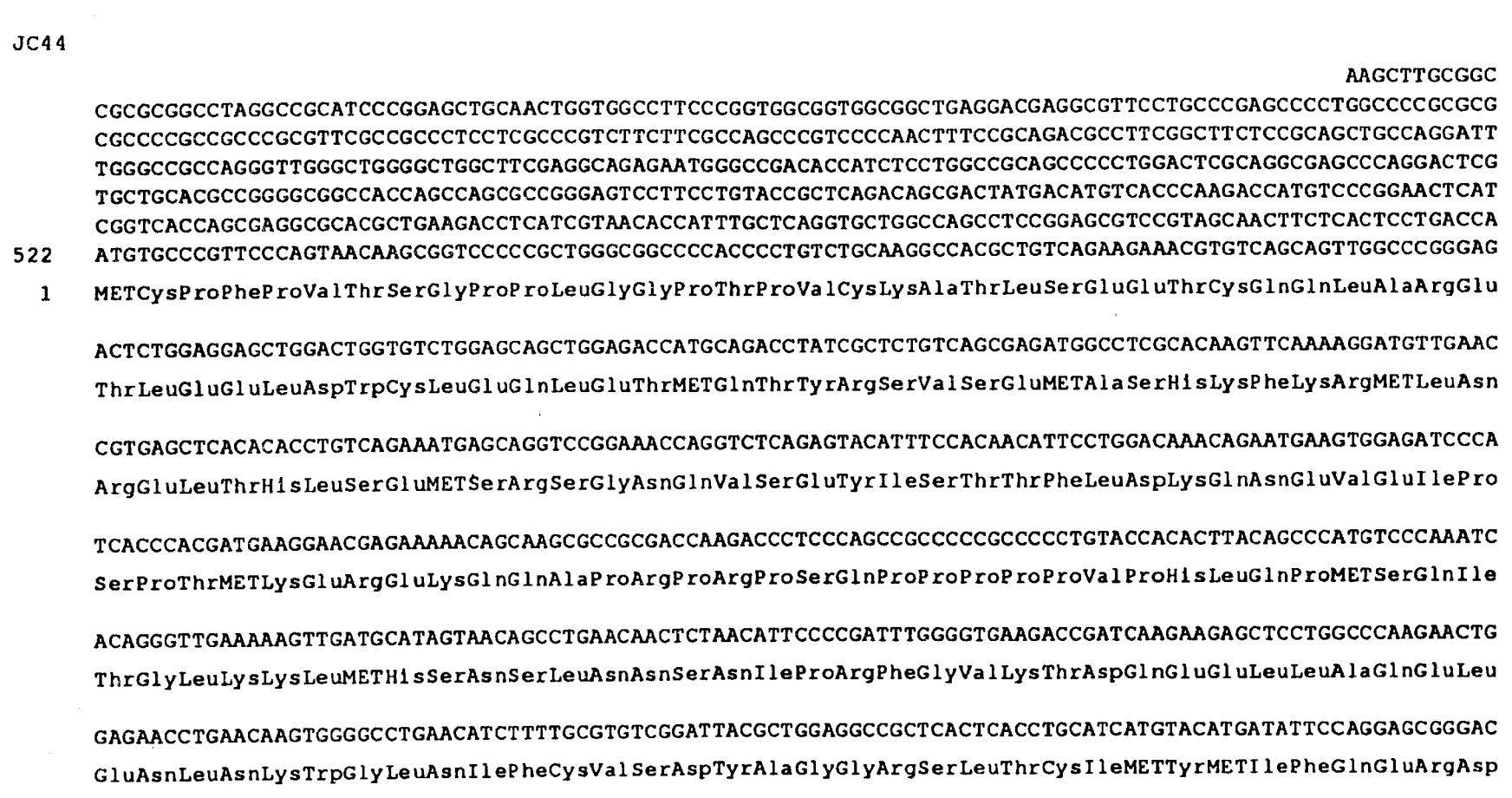

The present method has been used, as described in Examples 1 and 2, to isolate new mammalian genes whose presence in yeast cells has resulted in correction of a phenotypic alteration associated with a genetic alteration (the presence of the $RAS2^{val19}$ gene). The nucleotide sequences of these genes, as well as the amino acid sequence encoded by each, are described in Examples 1 and 2, and are shown in FIGS. 3–7. The genes of FIG. 3 and 4 are homologous to the D. melanogaster dunce gene. The gene of FIG. 3 has also been recently isolated by others using the D. melanogaster dunce, gene as probe (Swinnen, J. V., et al., Proc. Natl. Acad. Sci. 86: 5325 (1989)).

Screening and Identification of Agents which Alter cAMP Phosphodiesterase Activity In its most general form, the second part of the invention (pharmacological screening) is carried out as follows: It is possible to screen for agents that reduce or stimulate the activity of any mammalian protein whose presence or expression in an altered microbial host cell in which a genetic alteration is associated with an identifiable phenotypic alteration results in correction of the phenotypic alteration. Two types of screens are possible, and are illustrated in Examples 3 and 4.

The first type of pharmacological screen is applicable when the mammalian gene encodes a protein of known and assayable biochemical function. The mammalian gene is first expressed in a microbial host by utilizing an appropriate host expression vector of the type already described. Extracts of host cells are prepared, using known techniques; the cells are disrupted and their cellular constituents released. Crude cellular extract or purified mammalian protein is assayed for the known biochemical function in the presence of agents, the effects of which on the protein are to be assessed. In this manner, agents which inhibit or stimulate the activity of the mammalian protein can be identified.

This type of procedure can be carried out to analyze the effects of selected agents on mammalian cAMP phosphodiesterases. For example, a yeast strain lacking both endogenous PDE1 and PDE2 genes can be used as the host cell, into which cDNA encoding mammalian cAMP phosphodiesterase is introduced in an appropriate expression vector and expressed. Such a host cell is particularly useful because there is no background cAMP phosphodiesterase activity (Colicelli, J., et al., Proc. Natl. Acad. Sci. USA 86: 3599 (1989)) and hence activity of the mammalian enzyme can be cleanly assayed even in crude cell extracts. This procedure is illustrated in Example 3, in which it is demonstrated that the enzymatic activity of the rat DPD gene product is inhibited by the pharmacological agents Rolipram and RO20 1724, but not by the pharmacological agent theophylline.

The second type of pharmacological screen is applicable even when the mammalian gene encodes a protein of unknown function, and, thus, cannot be assayed by a biochemical activity. In this method, agents to be tested are applied or introduced directly to the genetically altered microbial host expressing the mammalian protein. Agents capable of inhibiting the mammalian gene or gene product are identified by their ability to reverse the phenotype originally corrected by expression of the mammalian protein in the altered host.

This procedure has been used for mammalian cDNAs encoding cAMP phosphodiesterases and a yeast containing $RAS2^{val19}$ as the host strain (see Example 4). This host is heat shock sensitive. When the rat DPD gene is introduced into the heat shock sensitive host and expressed, the host strain becomes resistant to heat shock. When the now resistant cells are incubated in Rolipram, they become heat shock sensitive again, indicating that Rolipram inhibits the activity of the rat DPD gene product. This pharmacological screen does not require that the function of the DPD gene product be known. This same approach can be applied to the genes which are the products of Example 2.

Applications of the Present Method and Products

The present method is useful for cloning novel mammalian genes which encode cAMP phosphodiesterases or proteins which interact with a RAS protein. As described, novel mammalian genes have been cloned, using the present method, and the amino acid sequence of the encoded protein has been deduced. Other mammalian genes encoding additional cAMP phosphodiesterases or additional proteins which interact with a RAS protein can be cloned using the method described. All or a portion of the sequence of the mammlaian genes encoding cAMP phosphodiesterases can be used as probes, in known techniques, to identify homologs and the products encoded by such assayed homologs as described herein for cAMP phosphodiesterase activity. Similarly, all or a portion of the mammalian genes encoding products which interact with RAS proteins can be used to identify homologs and the ability of the encoded proteins to interact with RAS proteins assessed as described herein.

Alternatively, mammalian genes encoding other proteins which function in an altered microorganism to correct, complement or supplement the altered or defective genetic activity can be cloned, using a microorganism with an appropriately-selected alteration (e.g., a change in a different biochemical pathway) which is associated with an identifiable phenotypic characteristic.

The present invention is also useful for identifying agents, particularly chemical compounds, which alter (reduce or stimulate) cAMP phosphodiesterase and, thus, affect cAMP activity (e.g., by causing more rapid cAMP breakdown or inhibiting cAMP breakdown and, thus, shortening or prolonging the duration of cAMP activity, respectively). The present method is also useful for identifying agents which alter (inhibit or enhance) the interaction of gene products with RAS proteins.

Antibodies specific for proteins encoded by the mammalian genes isolated using the present method can be produced, using known techniques. Such antibodies may be polyclonal or monoclonal and can be used to identify cAMP phosphodiesterases or proteins which interact with RAS proteins (e.g., the same proteins as those encoded by the mammalian genes or proteins sufficiently similar to the encoded proteins that they are recognized or bound by an antibody raised against the encoded proteins).

The present invention will now be illustrated by the following examples, which are not intended to be limiting in any way.

EXAMPLE 1

Identification of a Mammalian Gene that Can Revert the Heat Shock Sensitivity of RAS2$^{val119}$ Yeast Several yeast genes have been isolated which, when overexpressed on extrachromosomal yeast vectors, are capable of suppressing the heat shock sensitivity exhibited by the RAS2$^{val119}$ expressing strain TK161-R2V (Sass, P., et al., Proc. Natl. Acad. Sci. USA 83 (1986); Nikawa, J., et al., Mol. Cell. Biol., 7: 3629 (1987)). As described in this example, mammalian genes that can function in yeast to render RAS2$^{val119}$ cells resistant to heat shock have now been isolated. A rat brain cDNA library was produced and cloned into the yeast expression vector, pADNS (FIG. 1A). Double stranded cDNAs were prepared and ligated to NotI linkers, cleaved with NotI restriction enzyme, and cloned into pADNS at the NotI site situated between the alcohol dehydrogenase promoter and termination sequences of the vector. The use of the rare cutting NotI obviated the need for restriction site methylases commonly used in cDNA cloning.

Approximately $1.5 \times 10^5$ independent cDNA inserts were contained in the library, with an average insert size of 1.5 kbp. DNA prepared from the cDNA expression library was used to transform the RAS2$^{val119}$ yeast strain, TK161-R2V. 50,000 Leu$^+$ transformants obtained were subsequently tested for heat shock sensitivity. Only one transformant displayed heat shock resistance which was conditional upon retention of the expression plasmid. A plasmid, pADPD, was isolated from this transformant and the 2.17 kb NotI insert was analyzed by restriction site mapping and nucleotide sequencing (FIG. 2).

A large open reading frame of 562 codons was found. The first ATG appears at codon 46 and a protein which initiates at this codon would have a predicted molecular weight of approximately 60 kDa. This gene is designated DPD. A search for similar sequences was performed by computer analysis of sequence data banks, and the Drosophila melanogaster dunce gene was found. The two genes would encode proteins with an 80% amino acid identity, without the introduction of gaps, over a 252 amino acid region located in the center of the rat DPD cDNA. The dunce gene has been shown to encode a high affinity cAMP phosphodiesterase (Chen, C., et al., Proc. Natl. Acad. Sci. USA 83: 9313 (1986); Davis, R. L. and Kiger, J. A. J. Cell Biol. 90: 101 (1981); Walter, M. F. and Kiger, J. A. J. Neurosci. 4: 494 (1984)).

In order to demonstrate that the sequences upstream and downstream of the large sequence identity region were in fact contiguous with that region in the mRNA, rather than artifacts of the method for cDNA cloning, the structure of the cloned cDNA was compared with the structure of DPD cDNAs contained in an independently prepared, first strand CDNA population obtained by reverse transcribing total rat brain poly (A)$^+$ RNA with an oligo dT primer. Oligonucleotide primers complementary to sequences located within the identity region, and to sequences near the 5' or 3' ends of the coding strand, were made. Using either the cloned DPD DNA or the total first strand cDNA material as template, polymerase chain reactions (PCR) were carried out using four different primer sets and the reaction products were analysed by polyacrylamide gel electrophoresis. In each case, a fragment of the predicted length was obtained using either of the template DNAs. The band assignments were confirmed by cleavage with restriction endonucleases having recognition sites within the amplified DNA product. Again, in each case, the primary PCR product obtained using either source of template yielded cleavage products of the predicted sizes. The results indicate that the sequence arrangement in the cloned cDNA faithfully reflects the structure of the rat mRNA.

Expression and Characterization of the DPD Gene Product

S. cerevisiae encodes two cAMP phosphodiesterase genes, PDE1 and PDE2 (Sass, P., et al., Proc. Natl. Acad. Sci. USA 83: 9303 (1986); Nikawa, J., et al., Mol. Cell. Biol. 7: 3629 (1987)). The S. cerevisiae strain 10DAB carries disruptions of both of these genes. The resulting cAMP phosphodiesterase deficiency leads to elevated intracellular cAMP levels and a heat shock sensitivity phenotype similar to that of strains harboring the RAS$^{val119}$ allele (Nikawa, J., et al., Mol. Cell. Biol. 7: 3629 (1987). 10DAB cells were transformed with the DPD expression plasmid, pADPD, and assayed for heat shock sensitivity. Expression of the rat DPD gene indeed rendered this host resistant to heat shock.

In order to analyse the biochemical properties of the DPD gene product, crude cell extracts were prepared from one liter cultures of 10DAB which had been transformed with either pADNS or pADPD. Phosphodiesterase activity assays were performed using cAMP as substrate. Control extracts (10DAB with pADNS)showed no cAMP phosphodiesterase activity. Results with the controls were unchanged when performed at 0° C. or in the absence of Mg$^{2+}$ and were comparable to results obtained when no extract was added. These results indicate that there is no detectable background phosphodiesterase activity in strain 10DAB.

In contrast, considerable cAMP phosphodiesterase activity was seen in the 10DAB strain transformed with pADPD. The rate of cAMP hydrolysis in cells containing DPD was measured as a function of cAMP concentration. The deduced Km for cAMP is 3.5 $\mu$M and the calculated Vmax is 1.1 nmol/mg/min.

The assay conditions were varied in order to ascertain the cation preferences of the enzyme and to determine the ability of calcium and calmodulin to stimulate its activity. In these assays, $Mn^{2+}$ can be utilized as well as $Mg^{2+}$, and either cation in 1 mM final concentration was sufficient. Calcium/calmodulin was unable to stimulate the measured phosphodiesterase activity in the extract. A parallel assay using beef heart phosphodiesterase (Boeringer Mannheim) yielded a 6.5 fold stimulation with the addition of calcium/calmodulin. Finally, no cGMP phosphodiesterase activity was detected in these assays. Beef heart phosphodiesterase was again used as a positive control. In addition, cGMP present in amounts 100 fold over substrate concentrations was unable to inhibit cAMP phosphodiesterase activity.

Strains, Media, Transformations and Heat Shock

Escherichia coli strain HB101 was used for plasmid propagation and isolation, and strain SCS1 (Stratagene) was used for transformation and maintenance of the cDNA library (Mandel, M., and Higa, A. *J. Mol. Biol.* 53: 159 (1970); Hanahan, D. *J. Mol. Biol.* 166: 557 (1983)). Saccharomyces cerevisiae strain TK161-R2V (MAT a leu2 his3 ura3 trp1 ade8 can1 $RAS2^{va119}$) (Toda, T., et al., *Cell* 40: 27 (1985) and strain 10DAB were used. Strain 10DAB was created from a segregant of a diploid strain produced by mating TS-1 (Kataoka, T., et al., *Cell* 40: 19 (1985)) and DJ23-3C (Nikawa, J. I., et al., *Genes and Development* 1: 931 (1987)). The segregant (MATα leu2 his3 ura3 ade8 pde1::LEU2 pde2::URA3 ras1::HIS3) was subsequently transformed with the 5.4 kbp Xba1 pde1::ADE8 fragment of pYT19DAB to yield strain 10DAB. Yeast cells were grown in either rich medium (YPD) or synthetic medium with appropriate auxotrophic supplements (SC) (Mortimer, R. K. and Hawthorne, D. C. *In: The Yeast*, vol. 1 385 (1969)). Transformation of yeast cells was performed with lithium acetate (Ito, H., et al., *J. Bacteriol.*, 153: 163 (1983)). Heat shock experiments were performed by replica plating onto preheated SC plates which were maintained at 55° C. for 10 minutes, allowed to cool, and incubated at 30° C. for 24–48 hrs. Segregation analysis was performed by growing yeast transformants in YPD for 2–3 days, plating onto YPD plates, and replica plating onto YPD, SC-leucine (plasmid selection), and YPD heat shock plates.

Plasmids, DNA Manipulations, an Sequencing

Plasmid DNA from individual *E. coli* colonies was purified by standard procedures (Holmes, D. S., and Quigley, M. *Anal. Biochem* 114 193 (1981); Katz, L., et al., *J. Bacteriol.* 114 477 (1973). Extrachromosomal DNA was isolated from yeast as previously described (Nikawa, J. et al., *Mol. Cell. Biol.* 7: 3629 (1987)). The plasmid pYT19DAB was constructed from pYT19 (Nikawa, J. et al., *Mol. Cell. Biol.*, 7: 3629 (1987)) by first deleting PDE1 sequences between the SmaI and BalI restriction sites to yield pYT19D. The 4 kbp BamHI fragment of the ADE8 gene was then inserted into the BamHI site of pYT19D to yield pTY19DAB. The cloning vector pADNS is based on the plasmid pAD1 previously described (Powers, S., et al., *Cell* 47: 413 (1986)). pADNS consists of a 2.2 kbp BglII to Hpa1 fragment containing the *S. cerevisiae* LEU2 gene from YEp213 (Sherman, F., Fink, et al., *Laboratory Course Manual for Methods in Yeast Genetics*, eds. Sherman, F., Fink, G. R. and Hicks, J. B., Cold Spring Harbor Laboratory, Cold Spring Harbor, N.Y. (1986)), a 1.6 kbp HpaI to HindIII fragment of the *S. cerevisiae* 2 μ plasmid containing the origin of replication, and a 2.1 kbp SspI to EcoRI fragment containing the ampicillin resistance gene from the plasmid pUC18. It also contains a 1.5 kbp BamHI to HindIII fragment of the modified *S. cerevisiae* alcohol dehydrogenase (ADH1J) promoter (Bennetzen, J. L. and Hall. B. D. *J. Biol. Chem.* 257: 3018 (1982); Ammerer, G. *Meth. Enzymol.* 101: 192 (1983)) and a 0.6 kbp HindIII to BamHI fragment containing the ADH1 terminator sequences. The promoter and terminator sequences are separated by a polylinker that contains the restriction endonuclease sites NotI, SacII, and SfiI between the existing HindIII and SacI sites. The oligonucleotides used to create these sites were 5'- GGC-CAAAAAGGCCGCGGCCGCA and 5'- TCGACCG-GTTTTTCCGGCGCCGGCGTTCGA. The plasmid pADPD is a pADNS-derived plasmid containing the 2.17 kbp DPD cDNA insert.

Sequencing was performed using the dideoxy chain termination method (Sanger, R., et al., *Proc. Natl. Acad. Sci. USA* 74: 5463 (1977); Biggin, M. D., et al., *Proc. Natl. Acad. Sci. USA* 80: 3963 (1983)). Genalign was used to align the DPD and dunce sequences (GENALIGN is a copyrighted software product of IntelliGenetics, Inc.; developed by Dr. Hugo Martinez). RNA was purified from Sprague-Dawley rat brains by published procedures (Chirgwin, J. M. et al., *Biochem.* 18: 5294 (1979); Lizardi, P. M. *Methods Enzymol* 96: 24 (1983); Watson C. J. and Jackson J. F. *In: DNA cloning, a practical approach*, IRL Press Oxford (1984)). cDNAs were ligated to the NotI linker oligonucleotides 5'-AAGCGGCCGC and 5'- GCGGCCGCTT. The cDNAs were cleaved with NotI and cloned into the NotI site of pADNS using standard procedures.

Polymerase chain reactions (PCRs) were carried out in thermocycler (Perkin Elmer, Cetus) using a modification of published procedures (Saiki, R., et al., *Science* 239: 487 (1988)). Reaction mixtures contained template DNA (1 ng of cloned DNA, or 1 μg of total first strand cDNA), 25 pmoles of oligonucleotide primers, 200 μM deoxyribonucleotide triphosphates, 10 mM Tris HCl (Ph8.4), 50 mM KCl, 3 mM $MgCl_2$, and 0.01% (w/v) gelatin. The oligonucleotide primers used, as designated in FIG. 4, were:

A, 5'- CACCCTGCTGACAAACCT[44];

B, 5'-ATGGAGACGCTGGAGGAA[153];

C, 5'-ATACGCCACATCAGAATG[676l];

D, 5'-TACCAGAGTATGATTCCC[1449];

E, 5'-GTGTCGATCAGAGACTTG[1668] and

F, 5'-GCACACAGGTTGGCAGAC[2048]. The numbers indicate position coordinates in FIG. 3. Primers C, E and F are non-coding strand sequences. Thirty cycles (1.5 min at 94° C., 3 min at 55° C., and 7 min at 72° C.) were performed and the reaction products were analysed by polyacrylamide gel electrophoresis.

Phosphodiesterase Assays

Yeast cells were grown at 30° C. for 36 hours in one liter cultures of synthetic media (SC-leucine). Cells were harvested and washed with buffer C (20 mM MES, 0.1 mM $MgCl_2$, 0.1 mM EGTA, 1 mM β-mercaptoethanol), were resuspended in 30 ml buffer C with 50 μl 1M PMSF, and were disrupted with a French press. The extracts were centrifuged at 1,600 g for 10 min and the supernatants were spun at 18,000 g for 90 min (4° C.). The supernatant was assayed for phosphodiesterase activity (Sass, P., et al., *Proc. Natl. Acad. Sci. USA* 83: 9303 (1986); Nikawa, J., et al., *Mol. Cell. Biol.* 7: 3629 (1987)). All the reactions contained Tris-HCl (pH7.5) (100 mM), cell extract (50 μg protein/ml), 5'-nucleotidase (Sigma, 20 ng/ml) and 10 MM $Mg^{2+}$ (unless otherwise stated) and the indicated cyclic, nucleotide concentrations. Assays for the cGMP hydrolysis used 1.5 μM cGMP. Inhibition studies employed 5 μM cAMP in the presence of varying amounts of cGMP up to 500 μM. [$^3$H]cAMP and [$^3$H]cGMP were obtained from NEN (New England Nuclear). Reactions were incubated for 10 min at 30° C. and stopped with 5X stop solution (250 mM EDTA, 25 mM AMP, 100 mMcAMP).

Discussion

Previous workers have cloned a mammalian gene in yeast using a biological screen (Lee, M. G. and Nurse, P. *Nature* 327: 31 (1987)). In that case, a homolog to the cdc2 gene of *S. pombe* was cloned by screening a cDNA library for complementation of cdc2 mutants. In that library, the cDNAs were inserted proximal to the SV40 early T antigen promoter. In our work we have employed a library with mammalian cDNAs inserted into a yeast expression vector, proximal to a strong yeast promoter. In addition, we have employed NotI linkers for cDNA cloning, which allows the convenient subcloning of an entire insert library from one vector to another. We feel that this will be a generally useful approach for cloning genes from higher eukaryotes when functional screens are possible in yeast. This system is particularly useful for the cloning of other cAMP phosphodiesterases from mammals. The availability of yeast strains totally lacking endogenous cAMP phosphodiesterase activity will also facilitate the biochemical characterization of these new phosphodiesterases.

The mammalian DPD cDNA can encode a protein with a high degree of amino acid sequence identity (80%) with the predicted *D. melanogaster* dunce gene product over an extended region. The dunce gene has been shown to encode a high affinity cAMP phosphodiesterase required for normal learning and memory in flies (Chen, C., et al., *Proc. Natl. Acad. Sci. USA* 83: 9313 (1986); Davis R. L. and Kiger, J. A. *J. Cell Biol.* 90: 101 (1981); Walter, M. F. and Kiger, J. A. *J. Neurosci.* 4: 495 (1984)). Compared to the striking level of sequence identity between DPD and dunce, the sequence conservation among other known cAMP phosphodiesterases is scant (Charbonneau, H., et al., *Proc. Natl. Acad. Sci. USA* 83: 9308 (1986)). Therefore the DPD-dunce homology in the conserved region represents more than a constraint on sequences required for cAMP binding and hydrolysis, and suggests a conservation of interactions with other components.

Biochemical characterization of the DPD cDNA product expressed in yeast indicates that it is a high affinity cAMP specific phosphodiesterase, as is dunce (Davis, R. L. and Kiger, J. A. *J. Cell. Biol.* 90: 101 (1981); Walter M. F. and Kiger, J. A. *J. Neurosci.* 4 (1984)). In addition, DPD activity, as measured in our assays, is not stimulated by the presence of calcium/calmodulin. This property is shared with dunce and is distinct from some other phosphodiesterases (Beavo, J. A. In *Advances in second messenger and phosphorprotein research*, eds. Greengard, P. and Robinson, G. A., Raven Press, NY vol. 22 (1988)). The two proteins, DPD and dunce, thus appear to have similar biochemical characteristics. However, it should also be noted that DPD encodes a protein product which shows much less significant homology (35%) to dunce beyond the previously described highly conserved core region. These nonconserved sequences could result in an altered or refined function for this mammalian dunce homolog.

The DPD sequence encodes a methionine codon at position 46 and the established reading frame remains open through to position 563, resulting in a protein with a predicted molecular weight of 60 kDa. The same reading frame, however, is open beyond the 5' end of the coding strand (FIG. 2). At present, it is not known if the methionine codon at position 46 is the initiating condon for the DPD protein. The coding sequence is interrupted by three closely spaced terminator codons. However, the established reading frame then remains open for an additional 116 codons, followed by more terminator codons, a polyadenylation consensus signal and a polyadenine stretch. This 3' open reading frame could be incorporated into another dunce-like phosphodiesterase through alternate splicing.

Davis et al., (Davis, R. L. et al., *Proc. Natl. Acad. Sci. USA* 86: 3604 (1989)) have also isolated a mammalian dunce homolog from a rat brain cDNA library using standard nucleic acid hybridization techniques. The gene which they describe is indeed similar to, through distinct from, the DPD cDNA described here. Within the highly conserved region, as defined in this work, the predicted amino acid sequences of the two rat genes are 93% identical. This homology falls off dramatically, however, in the flanking regions which show amino acid identities of 60% (upstream) and 30% (downstream) and require the use of sequence gaps for optimum alignment.

EXAMPLE 2

Identification of a Human Gene that Can Revert the Heat Shock Sensitivity of RAS2$^{val119}$ Yeast A cDNA library was constructed in $\lambda$ZAP using NotI linkers. In this example, the cDNA derived from mRNA purified from the human glioblastoma cell line U118MG. Inserts from the $\lambda$ vector were transferred into two yeast expression vectors. One, pADNS, is as described before. The other, pADANS (see FIG. 2B), differs in that the mRNA expressed will direct the synthesis of a fusion protein: an N terminal portion derived from the alcohol dehydrogenase protein and the remainder from the mammalian cDNA insert. Thus, two mammalian cDNA expression libraries were constructed.

These libraries were screened, as in the previous example, for cDNAs capable of correcting the heat shock sensitivity of the *S. cerevisiae* host TK161-R2V. Several cDNAs were isolated and analysed by sequencing. Four different cDNA genes were thereby discovered, and their sequences are shown in FIGS. 4–7.

The gene of FIG. 4 (JC44) was shown by computer analysis to be homologous to the rat DPD gene. Biochemical analysis has proven that JC44 encodes a cAMP phosphodiesterase. The other genes, called JC99, JC265, and JC310, show no significant homology to previously isolated genes.

The genes of FIGS. 3 and 4 were shown to be able to correct the phenotypic defects of pde1⁻ pde2⁻ yeast strains. The genes of FIGS. 5–7 were unable to do so. Thus, it appears that the latter, genes do not encode cAMP phosphodesterases. Rather, these genes encode proteins of unknown function which appear to be able to correct phenotypic defects in yeast with activated RAS proteins.

Materials and Methods

Figure 2B:
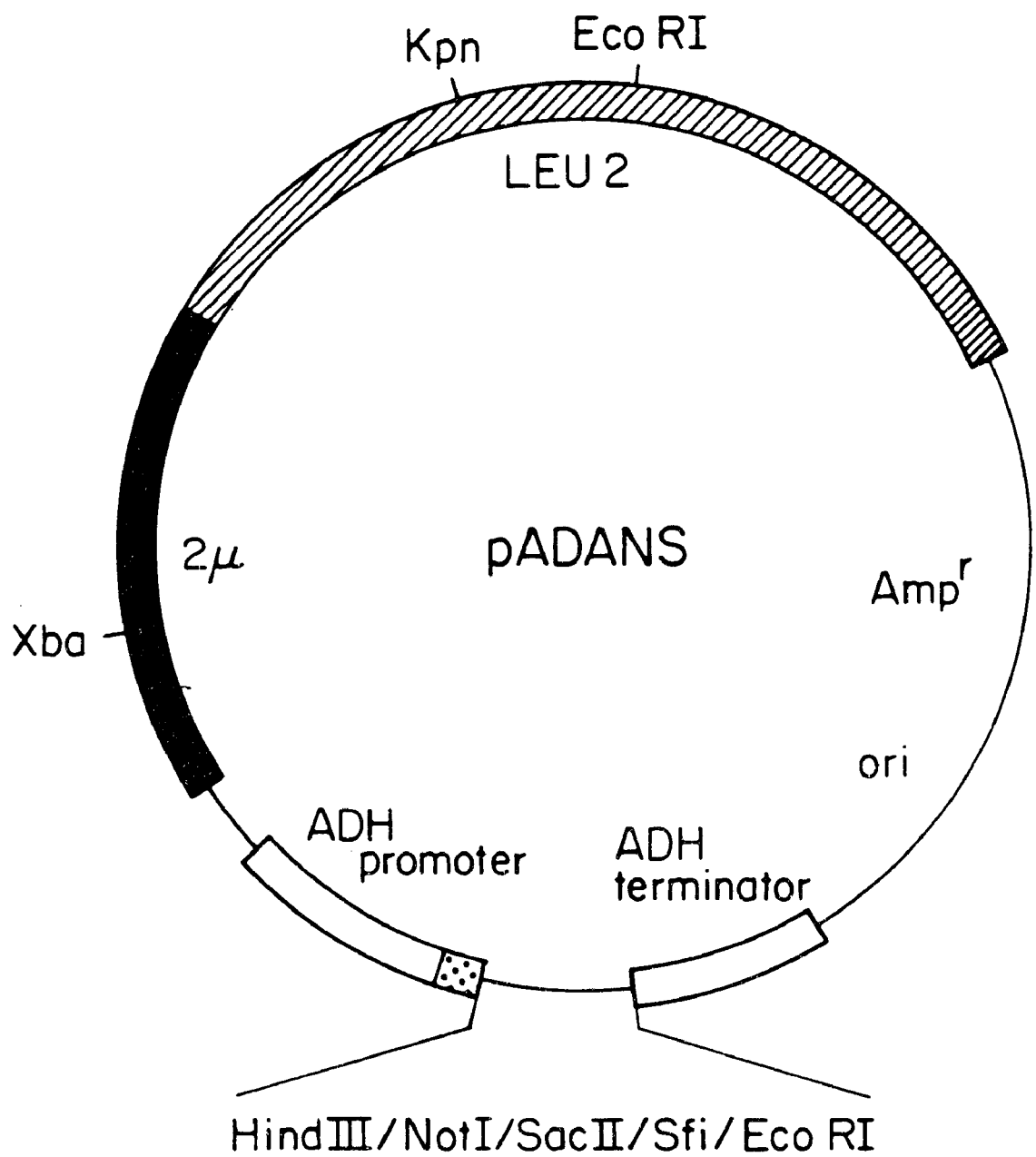
FIG. 2B is a schematic representation of yeast expression vector pADANS. The origins of replication (ori, 2 $\mu$) and selectable markers (AmpR, LEU2) are shown, as are the alcohol dehydrogenase (ADH) promoter and terminator sequences. The polylinker restriction endonuclease sites are as shown.

Procedures of Example 1 were followed throughout. Described here is the construction of the plasmid pADANS, shown in. FIG 2B. A PCR reaction was carried out on the yeast ADH1 gene in pJD14 (Bennetzen, J. L. and Hall, B. D. *J. Biol. Chem.* 257: 2018 (1982)). One oligonucleotide primer (5' TCTAAACCGTGGAATATT) was placed within the promoter region of the gene. The second primer (5' GTCAAAGCTTCGTAGAAGATAACACC) was designed to hybridize within the coding region of the gene. This primer included 5' non-hybridizing sequence encoding a HindIII endonuclease recognition site. The PCR product was then purified, digested with HindIII and EcoRV and ligated into the 8.0 kb HindIII and EcoRV (partial) digested fragment of pADNS. The resulting plasmid, pADANS, contains the entire ADH1 promoter and the first 14 amino acid codons of the ADH1 gene followed by the HindIII and NotI restriction endonuclease sites.

EXAMPLE 3

Identification of Agents which Inhibit Phosphodiesterase Activity

This example illustrates the use of the genes and cells described in Example 1 to identify chemical compounds which inhibit the activity of a known enzyme, the rat DPD phosphodiesterase. To test the efficiency of known inhibitory compounds, cell free extracts were made as described in Phosphodiesterase Assays. Yeast cells deficient in endogenous phosphodiesterase (10DAB), and expressing the rat DPD or yeast PDE2 genes from the described expression vector, were used. One liter cultures were harvested, washed in buffer C (20 mM MES/0.1 mM $MgCl_2$/0.1 mM EGTA/1 mM 2-mercaptoethanol), resuspended in buffer C containing 1.5 mM phenoylmethylsulfonyl fluoride, and disrupted in a French press at 4° C. Cell extracts were clarified at 100 g for 10 minutes and at 18000 g for 90 minutes. PDE activities were assayed as published (Saiki et al., *Science* 239: 487–491 (1988); Charbonneau et al., *Proc. Natl. Acad. Sci. USA* 83: 9308–9312 (1986); Tempel et al., *Proc. Natl. Acad. Sci. USA* 80: 1482–1486 (1983)) in a reaction mix containing 50 µg of cell protein/ml, 100 mM Tris (pH 7.5), 10 mM $Mg^{++}$ 5 µM cAMP, 5'-nucleotidase and [$^3$H] cAMP. Hydrolysed AMP was separated from cAMP using AG1-X8 resin from Bio Rad. About $10^4$ cpm were obtained for 10 minutes reactions and backgrounds (phosphodiesterase deficient-yeast or no extract) were about 300 cpm. The cytosolic fraction was assayed in the presence or absence of inhibitory compounds. These assays measure the amount of adenosine 5' monophosphate (AMP) produced by phosphodiesterase-catalysed hydrolysis of adenosine 3', 5'-cyclic adenosine monophosphate (cAMP). For each extract the percent inhibition for various concentrations of known inhibitors is given in Table 1. The percent inhibition represents the decrease in phosphodiesterase activity relative to measurements made in the absence of inhibitors. Rolipram, and the related compound RO20 1724, were the most effective inhibitors of DPD activity.

TABLE 1

Inhibition of Phosphodiesterases by Chemicals

| Phosphodiesterase | Agent | Concentration (µM) | Inhibition (%) |
|---|---|---|---|
| PDE2 | Theophylline | 250 | 0.0 |
|  | IBMX | 250 | 0.0 |
|  | RO20 1724 | 100 | 3.0 |
|  | Rolipram | 100 | 0.0 |
| DPD-1 | Theophylline | 250 | 42. |
|  | IBMX | 250 | 87. |
|  | RO20 1724 | 0.1 | 35. |
|  |  | 1.0 | 52. |
|  |  | 10.0 | 79. |
|  |  | 100.0 | 92. |
|  | Rolipram | 0.1 | 50. |
|  |  | 1.0 | 72. |
|  |  | 10.0 | 92. |
|  |  | 100.0 | 95. |

This analysis can, of course, be extended to test new or related chemical compounds for their ability to inhibit DPD activity, or the activity of another phosphodiesterase expressed in this system. Clearly, this form of analysis can also be extended to other genes cloned and expressed in a similar manner, for which there is an assayable enzymatic activity.

EXAMPLE 4

Figure 8:
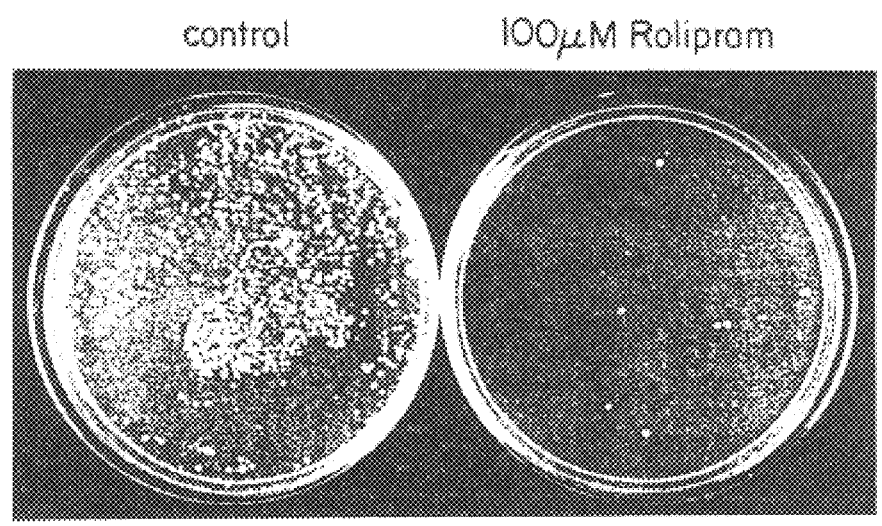
FIG. 8 shows suppression of heat shock resistance resulting from treatment of yeast cultures with a pharmacological agent. Cells on the right plate were pretreated with 100 $\mu$M rolipram prior to heat shock treatment.

Identification of Agents which Inhibit Mammalian Proteins of Unknown Function Expressed in Yeast This example illustrates the use of the genes and methods described to identify chemical compounds which inhibit the function of the encoded mammalian proteins expressed in yeast, even when the function of that protein is not known. 10DAB cells, which are phosphodiesterase deficient, are sensitive to heat shock. As already discussed, when these cells express DPD, they become resistant to heat shock. FIG. 8 demonstrates the inhibition of DPD function in yeast cells assayed by heat shock survival. 10DAB cells expressing DPD were maintained in rich medium (YPD) for three days at stationary phase. These cultures were then treated with rolipram, a known phosphodiesterase inhibitor, for 40 minutes at a final concentration of 100 µM. Control cultures were not treated with any inhibitor. These cultures were then heat shocked in glass tubes at 50° C. for 30 minutes. One microliter of each culture was plated. As shown in FIG. 8, cultures treated with rolipram (right side) were much more sensitive to heat shock, reflecting an inhibition of DPD enzymatic function.

Similarly, the suppression of heat shock sensitivity in the $RAS2^{va119}$ yeast strain (TK161-R2V) by DPD expression will also be inhibited by drug treatment. In addition, any other phenotype which is dependent on DPD phosphodiesterase activity should be affected by the presence of the inhibitory drug. The effect of a drug or agent can be assessed as described. Finally, in the most generalized case, inhibitory chemicals for proteins of unknown function, expressed from mammalian cDNAs in yeast, can be discovered in a similar way. This approach depends only on the phenotype consequent to expression of the protein and not on knowledge of its function.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

What is claimed is:

1. A method of identifying a chemical agent which alters activity of a protein encoded by a mammalian gene which, when expressed in genetically altered host cells, modifies a phenotypic alteration associated with a genetic alteration in the host cells, comprising the steps of:

(a) expressing the protein encoded by the mammalian gene in genetically altered host cells in which the protein encoded by the mammalian gene is not expressed, thereby modifying the phenotypic alteration associated with the genetic alteration;

(b) obtaining from genetically altered host cells produced in step (a) protein encoded by the mammalian gene;

(c) combining protein encoded by the mammalian gene with a chemical agent to be assayed for its ability to alter activity of the protein encoded by the mammalian gene; and (d) determining activity of the protein encoded by the mammalian gene in combination with the chemical agent.

* * * * *

UNITED STATES PATENT AND TRADEMARK OFFICE
CERTIFICATE OF CORRECTION

PATENT NO. : 6,569,617 B1
DATED : May 27, 2003
INVENTOR(S) : Michael H. Wigler et al.

It is certified that error appears in the above-identified patent and that said Letters Patent is hereby corrected as shown below:

<u>Title page,</u>
Item [57], ABSTRACT,
Line 7, replace "antibodies-which" with -- antibodies which --.
Item [56], References Cited, OTHER PUBLICATIONS, replace
"*J. Biol. Chem.*" with -- *J. Biol. Chem.*, --; replace "Reverse" with -- Reverses --; and replace "(17:" with -- (17): --.

<u>Column 2,</u>
Lines 1-2, replace "cAMP, phosphodiesterases" with -- cAMP phosphodiesterases --.

<u>Column 5,</u>
Line 38, replace "Advaces" with -- Advances --.

<u>Column 7,</u>
Line 21, replace "RAS2. (Kataoka, T., *et al.*," with -- RAS2 (Kataoka, T., *et al.*, --.

<u>Column 9,</u>
Line 54, replace "genes of Fig. 3 and 4" with -- genes of Fig. 3 and 4 --.
Line 57, replace "dunce, gene as probe" with -- dunce gene as probe --.
Line 59, replace "Screeningand" with -- Screening and --.

<u>Column 10,</u>
Lines 45-46, replace "now resistant" with -- now-resistant --.

<u>Column 13,</u>
Line 41, replace "an Sequencing" with -- and Sequencing --.

<u>Column 14,</u>
Line 37, replace "C, 5'-ATACGCCACATCAGAATG$^{6761}$" with
-- C, 5'-ATACGCCACATCAGAATG$^{676}$ --.
Line 60, replace "indicated cyclic, nucleotide" with -- indicated cyclic nucleotide --.

<u>Column 15,</u>
Line 53, replace "nonconserved" with -- non-conserved --.

<u>Column 16,</u>
Line 46, replace "latter, genes" with -- latter genes --.
Line 53, replace "shown in. FIG 2B." with -- shown in FIG 2B. --.

UNITED STATES PATENT AND TRADEMARK OFFICE
CERTIFICATE OF CORRECTION

PATENT NO. : 6,569,617 B1
DATED : May 27, 2003
INVENTOR(S) : Michael H. Wigler et al.

It is certified that error appears in the above-identified patent and that said Letters Patent is hereby corrected as shown below:

Column 17,
Line 17, replace "phenoylmethylsulfonyl" with -- phenylmethylsulfonyl --.
Line 24, replace "10mM $Mg^{++}$5 µM cAMP" with -- 10mM $Mg^{++}$, 5 µM cAMP, --.

Signed and Sealed this

Twenty-third Day of December, 2003

JAMES E. ROGAN
*Director of the United States Patent and Trademark Office*